(12) United States Patent
Clark et al.

(10) Patent No.: US 10,620,181 B2
(45) Date of Patent: Apr. 14, 2020

(54) METHOD OF ANALYSING A DRILL CORE SAMPLE

(71) Applicant: COREX (UK) LIMITED, Aberdeen (GB)

(72) Inventors: Brett Louis Clark, Aberdeen (GB); John Alexander Cumming Maitland, Aberdeen (GB); Ian Thomas Maurice Patey, Aberdeen (GB)

(73) Assignee: Corex (UK) Limited, Aberdeen (GB)

( * ) Notice: Subject to any disclaimer, the term of this patent is extended or adjusted under 35 U.S.C. 154(b) by 580 days.

(21) Appl. No.: 15/301,424

(22) PCT Filed: Apr. 2, 2015

(86) PCT No.: PCT/GB2015/051041
§ 371 (c)(1),
(2) Date: Oct. 3, 2016

(87) PCT Pub. No.: WO2015/150825
PCT Pub. Date: Oct. 8, 2015

(65) Prior Publication Data
US 2017/0108483 A1  Apr. 20, 2017

(30) Foreign Application Priority Data
Apr. 3, 2014 (GB) .................................. 1406039.6

(51) Int. Cl.
*G01N 33/24* (2006.01)
*G01N 15/08* (2006.01)
(Continued)

(52) U.S. Cl.
CPC ............. *G01N 33/24* (2013.01); *G01N 15/08* (2013.01); *G01N 23/046* (2013.01);
(Continued)

(58) Field of Classification Search
CPC ...... G01N 33/24; G01N 15/08; G01N 23/046; G01N 2223/305; G06F 17/5009
(Continued)

(56) References Cited

U.S. PATENT DOCUMENTS 4,799,382 A   1/1989  Sprunt et al.
5,164,590 A   11/1992 Coles et al.
(Continued)

FOREIGN PATENT DOCUMENTS

GB   2460786 B    11/2008
WO   2008132132 A1   11/2008
(Continued)

OTHER PUBLICATIONS

Nathalie_2012 (Mining a Massive Reservoir Engineering Database for Determinants of Recovery Efficiency; AES/PE/12-2, Jan. 24, 2012).*
(Continued)

*Primary Examiner* — Brian S Cook
(74) *Attorney, Agent, or Firm* — Gregory L. Porter; Hunton Andrews Kurth LLP

(57) ABSTRACT

A method of analysing a subterranean drilled core sample 10 is disclosed. The steps followed are: —a) providing a drill core sample 10 taken from a subterranean formation; b) producing high-resolution data of at least a section of the drill core sample 10 and creating a 3D before test skeleton of the sample 10 using that data; c) mimic wellbore operations using reservoir conditions core floods; d) producing high-resolution data of at least a section of the drill core sample 10 and creating a 3D after test skeleton of the sample using that data; e) identifying and/or segregating one or more formation damage mechanisms 12 by subtracting the 3D before test skeleton from the 3D after test skeleton to create a 3D change skeleton which shows all the formation
(Continued)

damage mechanisms 12; and f) 1) identify one or more individual formation damage mechanisms 12, by conducting segmentation including performing one or more diagnostic analysis techniques on at least a section of the drill core sample 10 and generating individual or combinations of simulated 3D skeletons; and 2) determining the effect of said formation damage mechanism(s) 12 on a chosen characteristic of interest of said drill core sample 10.

30 Claims, 19 Drawing Sheets

(51) Int. Cl.
  *G01N 23/046* (2018.01)
  *G06F 17/50* (2006.01)
(52) U.S. Cl.
  CPC ... *G06F 17/5009* (2013.01); *G01N 2223/305* (2013.01); *G01N 2223/401* (2013.01); *G01N 2223/616* (2013.01)
(58) Field of Classification Search
  USPC .......................................................... 703/10
  See application file for complete search history.

(56) References Cited

U.S. PATENT DOCUMENTS

| | | | |
|---|---|---|---|
| 5,253,719 A | | 10/1993 | Blauch et al. |
| 5,297,420 A | * | 3/1994 | Gilliland ................ G01N 15/08 73/38 |
| 5,493,226 A | | 2/1996 | Honarpour et al. |

FOREIGN PATENT DOCUMENTS

| | | |
|---|---|---|
| WO | 2009058390 A1 | 5/2009 |
| WO | 2012082797 A1 | 6/2012 |
| WO | 2013169137 A1 | 11/2013 |

OTHER PUBLICATIONS

Youssef 2007 (High Resolution CT and Pore-Network Models to Assess Petrophysical Properties of Homogeneous and Heterogeneous Carbonates, SPE-111427-PP 2007).*
Christian_2008 (Influence of Mechanical damage on fluid flow patterns investigated using CT scanning imaging and acoustic emissions techniques, Geophysical Research Letters, vol. 35, Issue 16 Aug. 2008).*
Nathalie_2012 (Mining a Massive Reservoir Engineering Database for Determinants of Recovery Efficiency; AES/PE/12-2, Jan. 24, 2012). (Year: 2012).*
Youssef_2007 (High Resolution CT and Pore-Network Models to Assess Petrophysical Properties of Homogeneous and Heterogeneous Carbonates, SPE-111427-PP 2007) (Year: 2007).*
Christian_2008 (Influence of Mechanical damage on fluid flow patterns investigated using CT scanning imaging and acoustic emissions techniques, Geophysical Research Letters, vol. 35, Issue 16 Aug. 2008). (Year: 2008).*
Grader_2009 (Computations of Porosity and Permeability of Sparic Carbonate Using Mutli-Scale CT images, SCA2009—Temp Papter #03-10). (Year: 2009).*
Search Report (GB1406039.6), dated Jun. 18, 2014.
Fleming, "Formation Damage", J. Petroleum Tech. (Feb. 2015), pp. 120-125.
Ling et al., "A New Approach to Estimate Invasion Radius of Water-Based-Drilling-Fluid Filtrate to Evaluate Formation Damage Caused by Overbalanced Drilling", SPE Drilling & Completion (SPE 168184) (Mar. 2015), pp. 27-37.
PCT Int'l Search Report (PCT/GB2015/051041), dated Aug. 10, 2015.

* cited by examiner

Key:

◯ Positive change

5mm

20mm

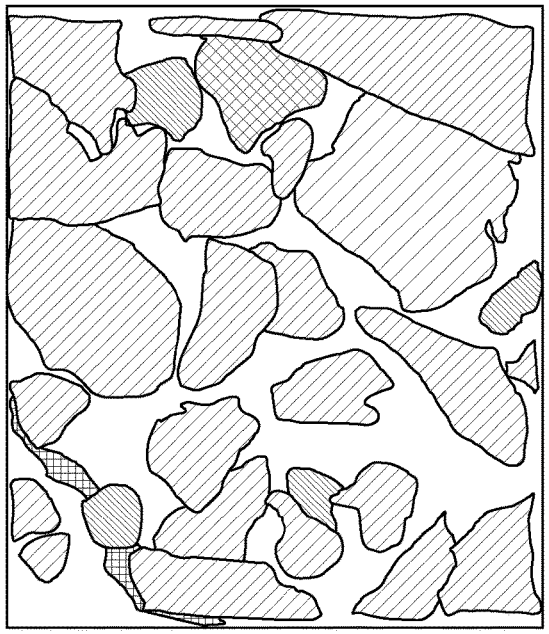 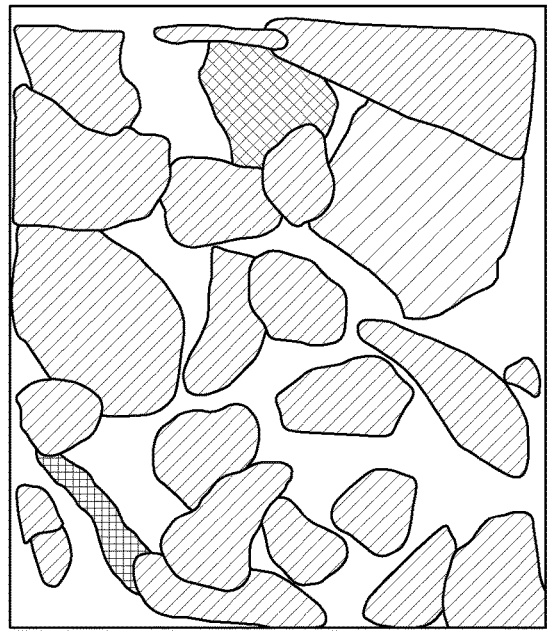
(a)     FIG. 12     (b)
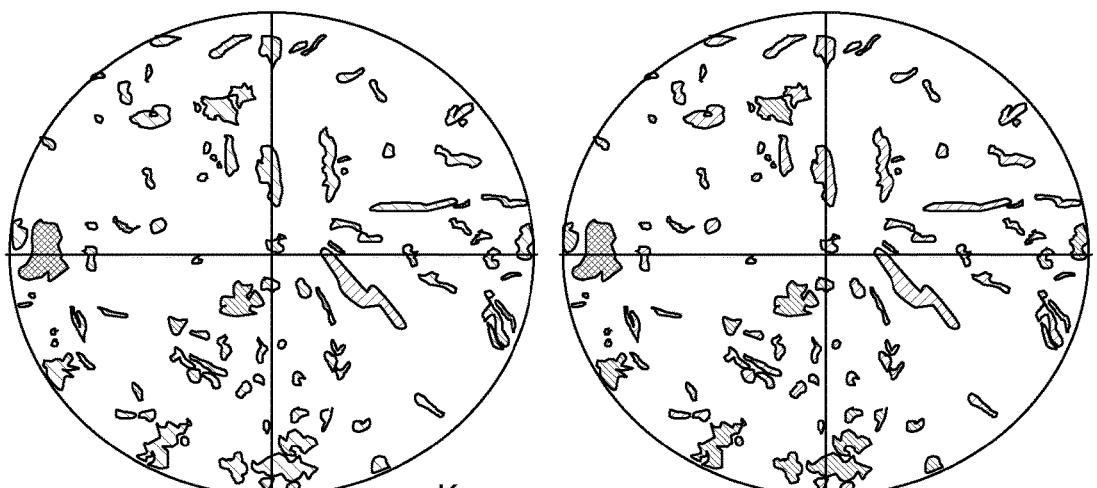
(a)     FIG. 13     (b)
Key:
- Dense fluid
- Kaolinite clay
- Pore network
- quartz FIG. 17
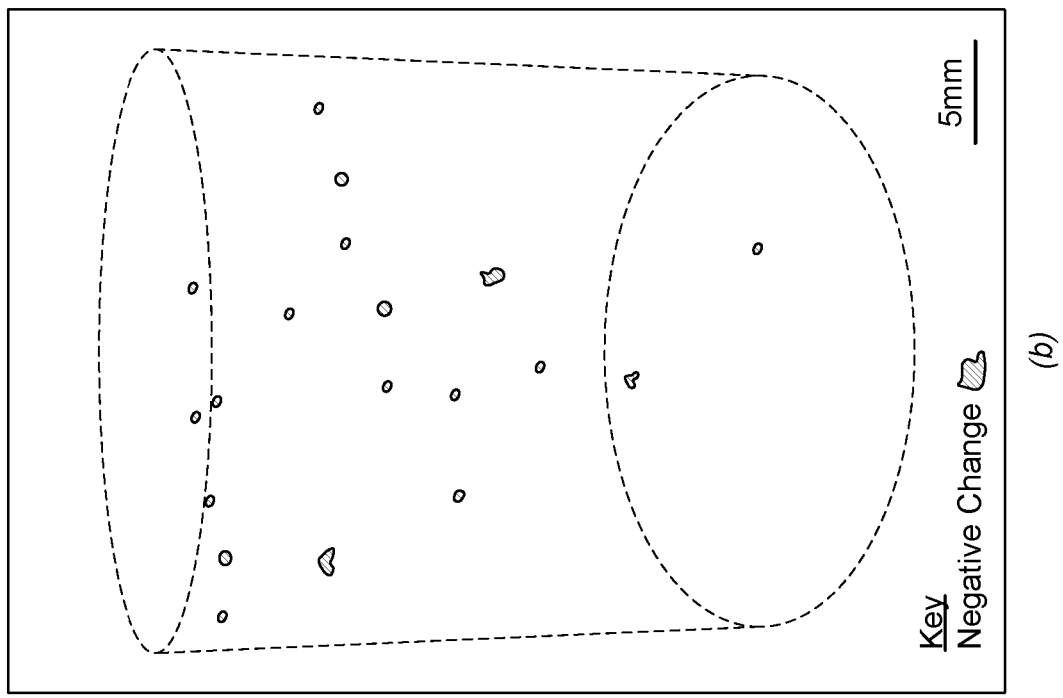
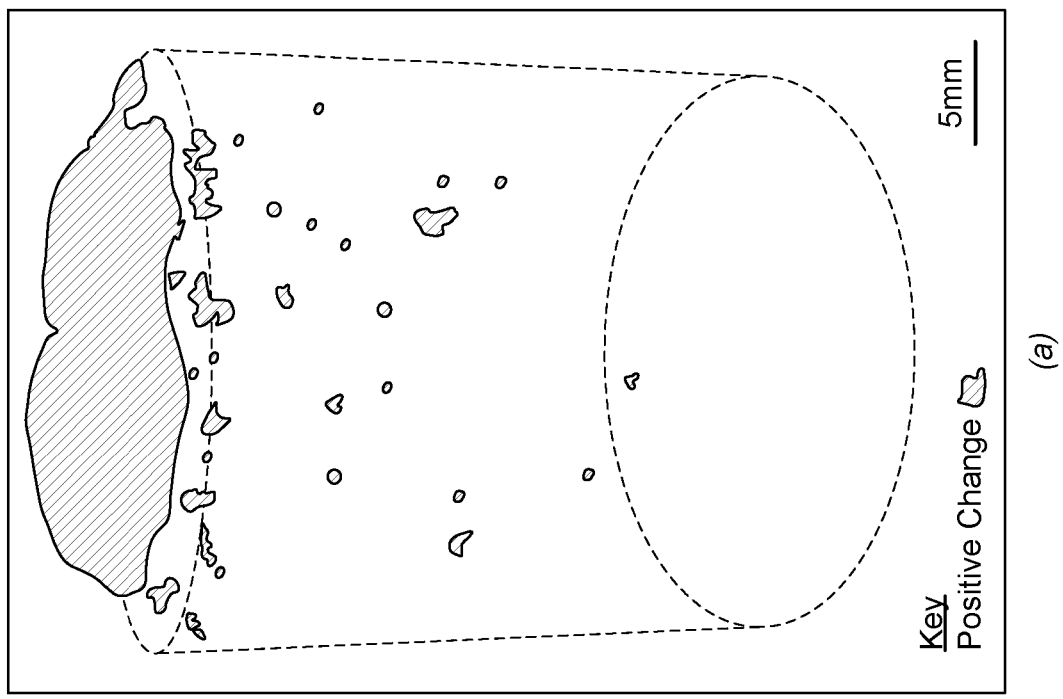

METHOD OF ANALYSING A DRILL CORE SAMPLE

The present invention relates to a method of analysing a drill core sample, in particular, to a method of analysing a subterranean drilled core sample.

The invention also relates to a method of quantification of formation damage mechanisms in a subterranean drilled core sample and the effect of the formation damage mechanisms on a characteristic (e.g. the permeability) of the core sample.

In oil and gas wells, valuable hydrocarbons locked in an underground reservoir are recovered to surface by drilling a wellbore into the formation and flowing the production fluids containing the valuable hydrocarbons to the surface through production tubing. "Production fluids" is a term used to refer to all fluids flowing from a production zone in the formation, and while production fluids flowing into the wellbore from the formation will normally contain a high proportion of usable hydrocarbons, they will usually also contain less useful components, such as particulate material comprising fine particles of sand, rock and fines etc, which may be suspended in the production fluids.

The efficient recovery of hydrocarbons relies on an accurate prediction of the transport parameters of reservoir rocks, in particular permeability.

Permeability impairment caused by damaging mechanisms in the reservoir, for example during well operations, can have a significant impact upon productivity, in particular, hydrocarbon recovery. Operational decisions are often influenced by the results of reservoir conditions tests, for example core flooding tests, which can be used to try and evaluate formation damage.

Formation damage testing is commonly used to gather information and aid in risk-reduction when making operational decisions. This is because the majority of damaging mechanisms can be simulated and replicated by performing reservoir conditions core flooding tests.

Formation damage laboratory testing is widely used to help understand the potential impact on productivity or injectivity of wellbore operations. Understanding what laboratory test results could mean in a field context is a key to reducing risk.

Interpretation of results has historically been dominated by taking permeability or pressure measurements at face value. The nature of laboratory testing means that it is a higher risk to rely on permeability and pressure measurements alone, so various geological techniques (including scanning electron microscopy and thin section) are used to gather additional information and aid interpretation. These geological techniques help reduce the inherent risk associated with upscaling from short core samples (including the potential for multiple mechanisms to be masking the potential for productivity impairment in the reservoir).

Examples of such techniques are disclosed in WO2013/058672, WO2013/169137, SPE 152640-PA: 'Permeability Upscaling for Carbonates From the Pore Scale by Use of Multiscale X-ray-CT Images', and SPE 165110-MS: 'Use of Micro-CT Scanning Visualisations To Improve Interpretation Of Formation Damage Laboratory Tests Including a Case Study From The South Morecambe Field'.

While the current techniques provide excellent high-resolution data, they are limited in terms of capturing the change throughout an entire core sample, particularly being able to capture the alterations and their distribution within samples.

Furthermore, permeability impairment is generally a result of a combination of formation damage mechanisms occurring during well operations. Current techniques are not able to segregate these formation damage mechanisms in order to measure permeability or determine their individual effects on the permeability.

Currently, there is no quantitative approach for estimating formation damage by making value-based measurements of damaging mechanisms. All known approaches are qualitative.

There is therefore a need for an improved method of analysing core samples that decreases risk in operational decision-making.

According to a first aspect, the present invention there is provided a method of analysing a subterranean drilled core sample, comprising
  a) providing a drill core sample taken from a subterranean formation;
  b) producing high-resolution data of at least a section of the drill core sample and creating a 3D before test skeleton of the sample using that data;
  c) mimic wellbore operations using reservoir conditions core floods;
  d) producing high-resolution data of at least a section of the drill core sample and creating a 3D after test skeleton of the sample using that data;
  e) identifying and/or segregating one or more formation damage mechanisms by subtracting the 3D before test skeleton from the 3D after test skeleton to create a 3D change skeleton which shows all the formation damage mechanisms; and
  f) 1) identify one or more individual formation damage mechanisms, by conducting segmentation including performing one or more diagnostic analysis techniques on at least a section of the drill core sample and generating individual or combinations of simulated 3D skeletons; and
     2) determining the effect of said formation damage mechanism(s) on a chosen characteristic of interest of said drill core sample.

Typically, the method comprises conducting steps a) to f) in turn.

The present invention provides an innovative quantitative technique to identify and segregate formation damaging mechanisms measuring permeability and/or further characteristics e.g. wettability or porosity of each core sample to allow the effects of any single or combination of formation damage mechanisms to be clearly understood.

The present invention also provides an improved analysis technique which overcomes the inability to separate and quantify the observed damaging mechanisms, as well as providing a novel value-based technique for improving hydrocarbon recovery and reduced risk decision-making for field operations.

The method in accordance with the invention uniquely utilises a combination of laboratory data with tools thus allowing visualisation of both the distribution and nature of damaging mechanisms. As a result, laboratory data is made more valuable and therefore decreases risk in operational decision-making.

Preferably, determining the effect of each identified individual formation damage mechanism on the chosen characteristic of interest of said drill core sample as well as the combined total effect of all of the formation damage mechanisms on the chosen characteristic of interest of said drill core sample such that the metric of each individual formation damage mechanism within the total formation damage quantified.

Typically, said determining step f) further comprises calculating the percentage volume of each formation damage mechanism. Optionally, step f) 1) further comprises generating a respective 3D skeleton of each formation damage mechanism combined with the 3D skeleton of the said section of the core sample (the latter being everything in the said section of the core sample which did not experience change) to provide an indication of the percentage volume or mass change. Preferably, the 3D skeletons are computer generated and the effect of said formation damage mechanisms is determined through the use of computer based permeability simulations on the said computer generated 3D skeletons of said drill core sample.

Preferably, step b) and/or step d) comprises producing high resolution data of the entire drill core sample.

Preferably, the chosen characteristic of interest comprises one of permeability or porosity or volume change such that step f) comprises determining the effect of said formation damage mechanism(s) on the said one of effective permeability or porosity or volume loss of the drill core sample.

Preferably, step f) comprises determining the effect of said formation damage mechanism(s) on the permeability of the drill core sample.

The determining step f) may further comprise calculating a volume change in said drill core sample caused by each of the one or more formation damage mechanisms.

In exemplary embodiments, the determining step f) further comprises calculating a volume change in said drill core sample caused by a combination of different formation damage mechanisms.

The method may further comprise generating individual or combinations of 3D skeletons representing formation damage mechanism(s), grain(s) and pore space(s) by segmentation.

In exemplary embodiments, the determining step f) comprises calculating the percentage volume of each formation damage mechanism.

The formation damage mechanism may include fines accumulation and/or drilling solid retention.

In exemplary embodiments, the determining step f) further comprises:—
  i) dividing a selected area of interest of the core sample into two or more sub-sampling sections,
  ii) producing very high resolution data, and more preferably, at a higher resolution than the said high resolution utilised in either or both of steps b) and/or d), data of one or more sub-sampling sections, and
  iii) obtaining elemental analysis/chemical characterization of at least one of the sub-sampling sections and more preferably more than one and most preferably all of the sub-sampling sections.

Preferably, the core sample is divided into a plurality (such as 12-16) of sub-sampling sections.

Preferably, the high resolution data of step b) and/or step d) and the higher resolution data of step f) is produced by a suitable 3D dataset acquisition method for example but not limited to nano CT scanning, XRM, FIB, micro CT scanning or synchnotron analysis.

Preferably, step f) iii) obtaining elemental analysis/chemical characterization of at least one of the sub-sampling sections further comprises determining what change in said smaller segmented areas is attributable to what formation damage mechanism, and further comprises:— iv) constructing further 3D skeletons comprising a combination of the 3D change skeleton of step e) being combined with one or more of the simulated 3D skeletons of step f) 1). The elemental analysis/chemical characterization of step f) iii) may be obtained by a Focussed Ion Beam Scanning Electron Microscope (FIB-SEM) used in combination with an Energy-dispersive X-ray Spectroscopy device (EDS). This allows a user such as a consultant to acquire a chemical element map of an area of interest selected and therefore identify the formation damage mechanisms present.

Preferably, features of the sub-sampling sections in the very high resolution data of step f) ii) and features of the sub-sampling section obtained from data derived from the elemental analysis/chemical characterization of step f) iii) are matched via registration or point matching.

In exemplary embodiments, the method further comprising the step of extrapolating the formation damaging mechanisms captured in the FIB-SEM/EDS selected area of interest to have similar occurrences rendered elsewhere throughout the core sample dataset.

Preferably, step c) comprises mimicking (e.g. attempting to simulate) reservoir conditions by means of a test conducted on the core sample, for example a core flooding test.

In embodiments wherein step c) comprises a reservoir conditions test, high resolution data of the entire drill core sample is produced (prior to the reservoir conditions test of step c)) at step b) in order to produce before test data sets and/or scans.

One or more high resolution after test data sets and/or scans of the entire drill core sample may be produced at step d) (after the reservoir conditions test of step c)) and may be further additionally produced during various further stages of the test sequence depending on objectives in order to produce one or more after test data sets and/or scans as part of step e).

Preferably, change maps are generated to facilitate the identification and/or segregation of one or more formation damage mechanisms in step e).

Preferably the process of generating the change maps comprises the following steps:—
  overlaying and aligning the before and after test data sets;
  point wise intensity subtraction of the after test data sets from the before test data sets;
  change map image processing to produce a change map; and
  quantification of the data and change map.

Preferably the change map image processing step comprises processing change intensity data obtained from the point wise intensity subtraction step to produce the change map. Optionally, positive and negative change intensity can be separated in the change map.

Preferably, the quantification of the data and change map comprises the creation of a new data set using a binerization function. The binerization function conveniently attributes a value of 1 to both high and low intensity changes and attributes a value of 0 for no change. In this way, all change within the sample will be accounted for.

According to a second aspect, there is provided a method of quantification of formation damage mechanisms in a subterranean drilled core sample and the effect of the formation damage mechanisms on the characteristics (e.g. permeability) of the core sample comprising the steps of analysing a subterranean drilled core sample in accordance with the first aspect.

According to a third aspect, there is provided a database on formation damage mechanisms comprising a list of formation damage mechanisms and their effect on an analysed subterranean drilled core sample populated by data obtained by the method according to the first aspect.

In exemplary embodiments, the database further comprises a list of at least one compound characteristic(s) (e.g. permeability) impairment mechanism and the effect of the at least one compound characteristic(s) (e.g. permeability) impairment mechanism on an analysed subterranean drilled core sample, wherein the at least one compound characteristic(s) (e.g. permeability) mechanism comprises at least two different formation damage mechanisms and the list is populated by data obtained by the method according to the first aspect.

The various aspects of the present invention can be practiced alone or in combination with one or more of the other aspects, as will be appreciated by those skilled in the relevant arts. The various aspects of the invention can optionally be provided in combination with one or more of the optional features of the other aspects of the invention. Also, optional features described in relation to one aspect can typically be combined alone or together with other features in different aspects of the invention.

Various aspects of the invention will now be described in detail with reference to the accompanying figures. Still other aspects, features, and advantages of the present invention are readily apparent from the entire description thereof, including the figures, which illustrates a number of exemplary aspects and implementations. The invention is also capable of other and different examples and aspects, and its several details can be modified in various respects, all without departing from the spirit and scope of the present invention. Accordingly, the drawings and descriptions are to be regarded as illustrative in nature, and not as restrictive. Furthermore, the terminology and phraseology used herein is solely used for descriptive purposes and should not be construed as limiting in scope. Language such as "including", "comprising", "having", "containing", or "involving" and variations thereof, is intended to be broad and encompass the subject matter listed thereafter, equivalents, and additional subject matter not recited, and is not intended to exclude other additives, components, integers or steps. Likewise, the term "comprising" is considered synonymous with the terms "including" or "containing" for applicable legal purposes.

Any discussion of documents, acts, materials, devices, articles and the like is included in the specification solely for the purpose of providing a context for the present invention. It is not suggested or represented that any or all of these matters formed part of the prior art base or were common general knowledge in the field relevant to the present invention.

In this disclosure, whenever a composition, an element or a group of elements is preceded with the transitional phrase "comprising", it is understood that we also contemplate the same composition, element or group of elements with transitional phrases "consisting essentially of", "consisting", "selected from the group of consisting of", "including", or "is" preceding the recitation of the composition, element or group of elements and vice versa.

All numerical values in this disclosure are understood as being modified by "about". All singular forms of elements, or any other components described herein are understood to include plural forms thereof and vice versa. References to directional and positional descriptions such as upper and lower and directions e.g. "up", "down" etc. are to be interpreted by a skilled reader in the context of the examples described and are not to be interpreted as necessarily limiting the invention to the literal interpretation of the term, but instead should be as understood by the skilled addressee.

The following definitions will be followed in the specification. As used herein, the term "wellbore" refers to a wellbore or borehole being provided or drilled in a manner known to those skilled in the art. The wellbore may be 'open hole' or 'cased', being lined with a tubular string. Reference to up or down will be made for purposes of description with the terms "above", "up", "upward", "upper" or "upstream" meaning away from the bottom of the wellbore along the longitudinal axis of a work string and "below", "down", "downward", "lower" or "downstream" meaning toward the bottom of the wellbore along the longitudinal axis of the work string. Similarly 'work string' refers to any tubular arrangement for conveying fluids and/or tools from a surface into a wellbore.

BRIEF DESCRIPTION OF THE DRAWINGS

A detailed description of certain examples of the present invention follows, with reference to the attached drawings, wherein:

FIG. 12 schematically illustrates an example of high resolution 500× magnification SEM image region and registered region of nano-CT 3D image created during segmentation;

FIG. 13 schematically illustrates an example of filtering and boundary interfacing via 'water shedding' or segmentation;

FIG. 17A schematically illustrates a 3D representation of the positive change produced during stage 2.3; and FIG. 17B schematically illustrates a 3D representation of the negative change produced during stage 2.3.

DETAILED DESCRIPTION

A method of analysing a subterranean drilled core sample 10 (hereinafter referred to as the 'core sample') for the quantification of formation damage mechanisms 12 in the core sample 10 and the effect of the formation damage mechanisms 12 on the characteristics (e.g. permeability) of the core sample 10 in accordance with the invention will be described with reference to the figures.

Prior to following the method in accordance with the present invention, a core sample 10 is obtained from a subterranean formation 2.

The exemplary method in accordance with the present invention comprises the primary steps of:
  a) providing a drill core sample 10 taken from a subterranean formation 2;
  b) producing high resolution data of at least a section of the core sample 10, and preferably the whole core sample 10 (to provide a before test data set) and creating a 3D before test skeleton of the core sample 10 using that data;
  c) mimic wellbore operation using reservoir conditions core flooding test or other suitable test;
  d) producing high-resolution data of at least a section of the core sample 10, and preferably the whole core sample 10 (to produce an after test data set) and creating a 3D after test skeleton of the sample using that data;
  e) identifying and/or segregating one or more formation damage mechanisms 12 by subtracting the 3D before test skeleton of step b) above from the 3D after test skeleton of step d) above to create a 3D change skeleton which shows all the formation damage mechanisms; and
  f) 1) identifying one or more individual formation damage mechanisms 12, by conducting segmentation including performing one or more diagnostic analysis techniques on at least a section of the drill core sample 10 and generating individual or combinations of simulated 3D skeletons; and
    2) determining the effect of said formation damage mechanism(s) 12 on a chosen characteristic of interest (such as the permeability) of said core sample 12.

The characteristic of the core sample 12 is for example one or more characteristic(s) (e.g. permeability) of the core sample 12 but may be another characteristic of the core sample 12 such as wettability or porosity but is not limited to those.

Figure 1:
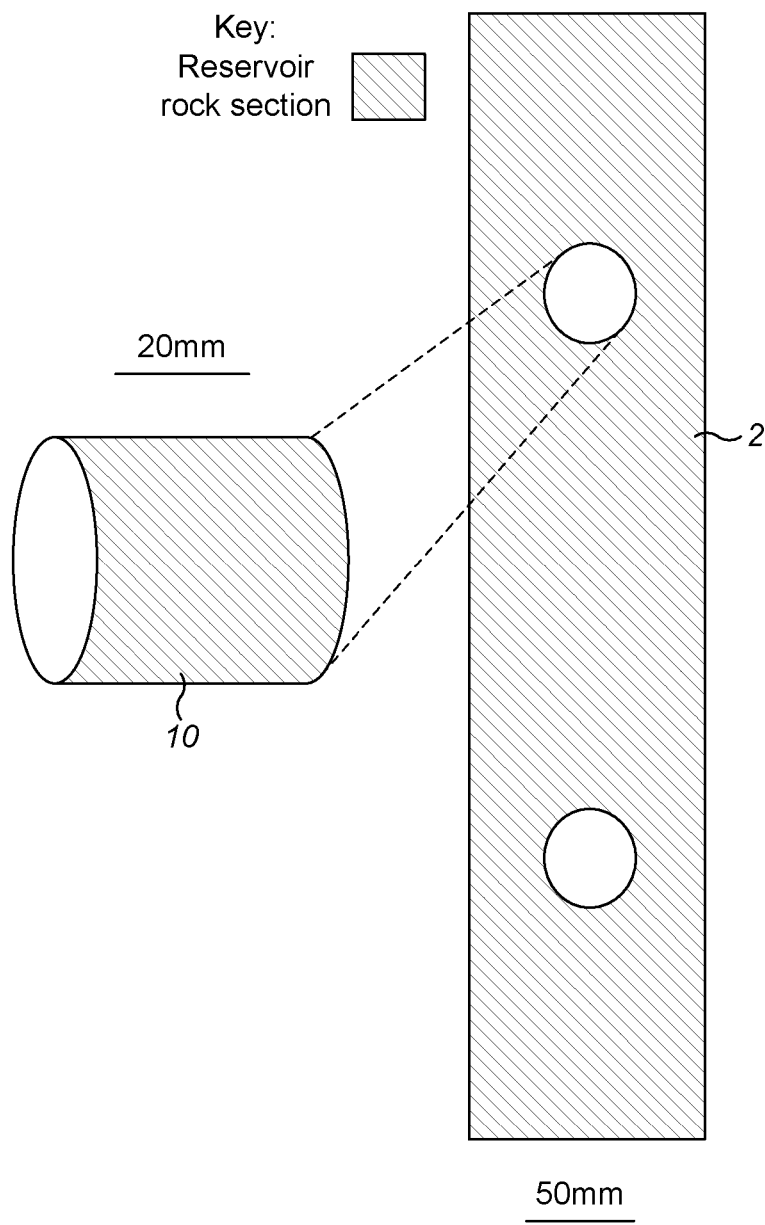
FIG. 1 schematically illustrates where a test core sample may be plugged (obtained) from a reservoir interval.

The core sample 10 will be obtained from a subterranean formation 2 in the form of a section of the reservoir rock (usually the hydrocarbon recovery interval/zone or hydrocarbon bearing zone). The core sample 10 is a cylinder which is normally in the region of 1 inch (2.54 cm) or 1.5 inches (3.81 cm) in diameter and up to 4 cm in length but other sizes of core samples 10 can be obtained and used. FIG. 1 shows an example of where a test core sample 10 may be plugged (obtained) from a reservoir interval 2.

The method of obtaining of a test core sample from a subterranean formation is typically achieved by using a conventional core barrel tool (not shown) at the lower end of a drill string run from the surface of a well using known techniques and is therefore generally known to the skilled person and as such will not be described in any further detail.

It would be understood that the core sample 10 may be of a different size, shape or dimension to that described above.

Extra geological analyses material is taken from the same depth as the core sample 10 for petrographic characterisation when the core sample obtained. The petrographic characterisation consists of X-ray diffraction (XRD) and/or scanning electron microscopy (SEM) analysis and/or other suitable petrographic or biological characterising analysis techniques. The petrographic or biological characterisation may be performed prior to (for example with a handheld tool or downhole tool included in the string with the core barrel and operated as the core sample 10 is taken or cut from the reservoir or just after) or during (e.g. in the laboratory) one of the main stages of investigating the effect of the formation damage mechanisms 12 on the characteristics (e.g. permeability) of the core sample 10 in the method in accordance with the invention.

The XRD and SEM analysis will allow a consultant (who may be for example, but not limited to, a geologist or micro-biologist or chemist) making the investigation to assess the minerals and clays present in the core sample 10.

The main stages of investigating the effect of the formation damage mechanisms 12 on the characteristics (e.g. permeability) of the core sample 10 in the method in accordance with the invention will now be described.

Stage 1—Core Preparation and Reservoir Conditions Tests (in Accordance with Steps a) to d))

Once the core sample 10 has been obtained (in accordance with step a)), the first stage of the investigation typically begins with preparing the core sample 10 for testing.

The core sample 10 is cleaned and re-prepared to a base line saturation profile using brine, oil or gas phase that is representative of the reservoir.

The core sample 10 is then stored at an appropriation temperature depending on the test phases, ageing may be undertaking to improve the conditioning of the core sample 10 to initial wellbore saturation.

The bulk test core sample 10 is then scanned by a suitable 3D dataset acquisition technique such as for example, but not limited to, nano-CT scanning, XRM, FIB, micro CT scanning or synchrotron analysis, before testing begins in order to produce before test 3D data set acquisition technique scans (B) (in accordance with step b)) where the data produced from such scans is loaded into suitable 3D skeleton visualisation software as will be detailed subsequently. Bulk volume scans will vary in resolution depending on core sample size but will usually be able to discern particle sizes down to a range between 18-26 μm (with e.g. nano CT although it should be noted that XRM can with present day (i.e. calendar year 2014) technology discern particle sizes down to a range of 2.5 to 26 μm and it is likely that future technology advancements will discern even lower particle sizes and therefore perform higher resolution scans) and therefore provides a high resolution scan.

The laboratory reservoir conditions test can now begin (in accordance with step c)). Testing of core samples 10 will mimic well operations e.g. fluid sequence applications and clean up, as well as any production and/or injection stages. The performance of the laboratory reservoir conditions test may be in accordance with any of the currently known methods, a common conditions test being for example a core flooding test.

The core sample 10 can be offloaded at specific stages during the mimicking of well operations to be scanned by a suitable 3D dataset acquisition technique to thereby provide one or more after test scans (A) (in accordance with step d)) to produce an after test data set. This can be done multiple times during various stages of the test sequence depending on the objectives. These after test 3D dataset acquisition technique scans (A) alongside the before test 3D dataset acquisition technique scans (B) made prior to simulating wellbore operations are processed using 3D imaging/image processing software capable of data visualization and analysis to produce respective after test (A) and before test (B) 3D skeletons within the 3D imaging/image processing software.

The 3D imaging/image processing software may be an off the shelf software package available to the skilled person for example an Avizo® software package or a specially developed and suitable software package.

Stage 2—Change Mapping 3D Dataset Acquisition Technique Bulk Sample Scans (in Accordance with Step e))

Figure 2:
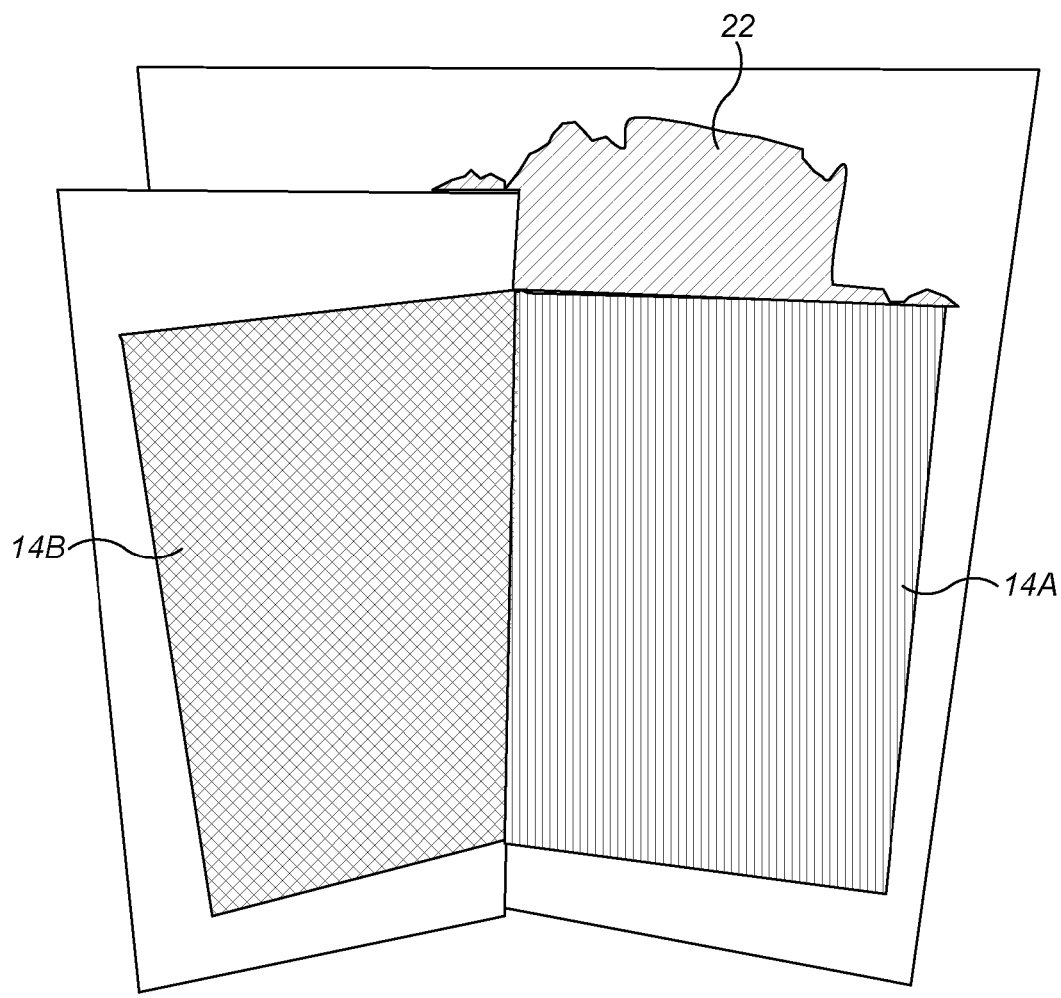
FIG. 2 schematically illustrates the alignment of the before and after test data after registration.

The 3D dataset acquisition technique data sets 14 obtained from the before test (B) and from each after test (A) 3D dataset acquisition technique scan conducted during stage 1 as outlined above are uploaded into the 3D image processing software and orthoslices can be used to view the data set and 3D skeletons can be created from the appropriate combination of the slices. FIG. 2 depicts an example of a before test (B) scan slice 14B with an intersecting after test (A) scan slice 14A (this includes the well operations deposited cake 22 and body at the top of the sample 10).

3D skeleton change maps (C) are generated by taking the after test (A) 3D dataset acquisition technique scans and subtracting the before test (B) 3D dataset acquisition technique scans (i.e. A-B=C).

The process of generating the change maps are outlined in more detail by the four stages listed below:

2.1—Registration (overlaying and aligning the before and after test data sets)
2.2—Arithmetic (Point wise intensity subtraction) [A−B]
2.3—Change map image processing [C]
2.4—Quantification 2.1 Registration Stage:—

Figure 3:
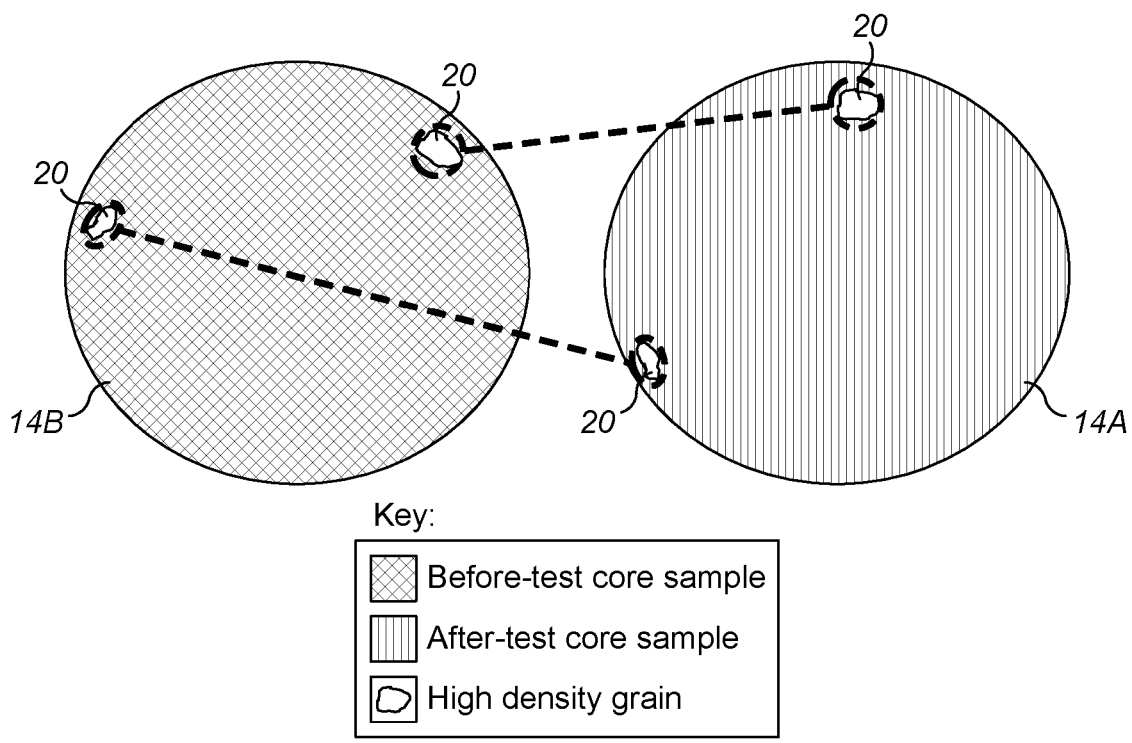
FIG. 3 schematically illustrates an example of corresponding features of a core sample in before and after test data sets produced by e.g. XRM or nano CT or FIB or micro CT or synchnotron analysis.

Both of the 3D skeletons for the before (B) and after (A) test 3D dataset acquisition technique data sets 14 have to be aligned together, such that the after test (A) 3D dataset acquisition technique data set 14A moves along the X, Y and Z axis into alignment with the before test (B) 3D dataset acquisition technique data set 14B. All grains 20, clays and cements are aligned together, between both 3D dataset acquisition technique data sets 14. See FIG. 3 for an example of corresponding features that are misaligned, which need to be corrected; this is done by registration.

The registration function is accomplished by having the after test (A) 3D dataset acquisition technique data set 14A registered to the before test (B) data set 14B. In simple terms the before test (B) 3D dataset acquisition technique data set 14B remains still and the after test (A) 3D dataset acquisition technique data set 14A moves, and as such the after test (A) data set 14A is aligned to the before test data (B) data set 14B.

Figure 4:
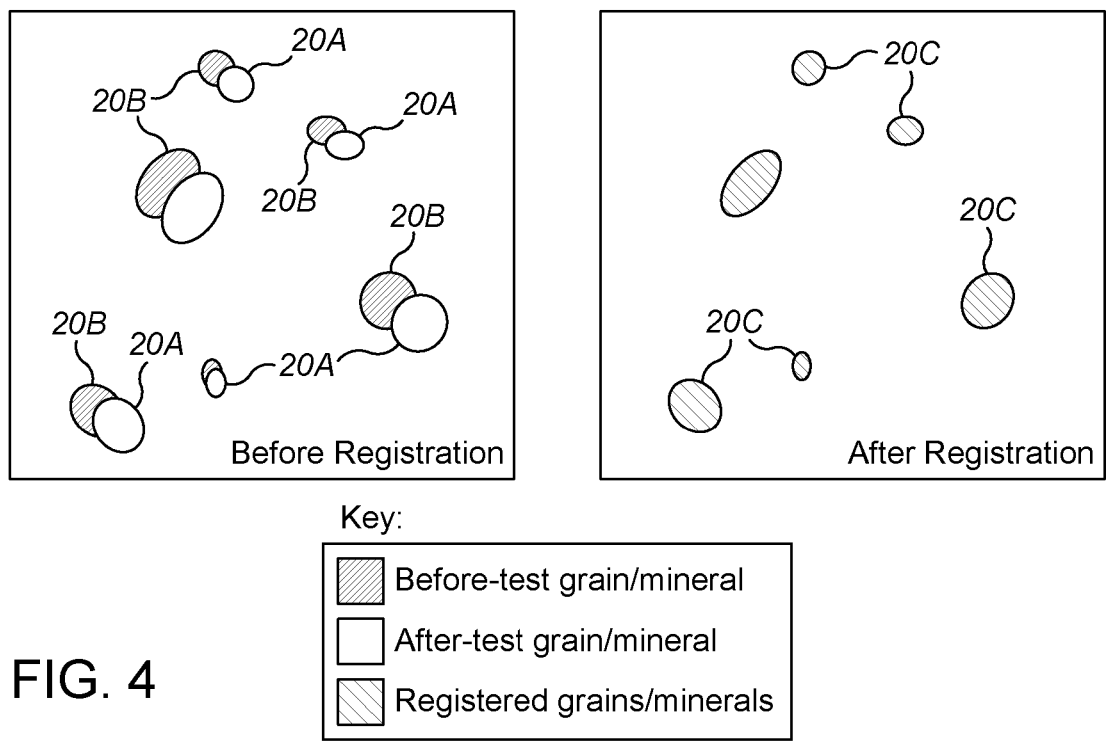
FIG. 4 schematically illustrates the registration of before and after test nano-CT data sets.

An illustration is depicted in FIG. 4 to show how registration works; black blobs represent high intensity grains/minerals 20 in the before test (B) data set 14B and white blobs represent high intensity grains/minerals 20 in the after test (A) data set 14A. The picture to the right shows grains/minerals are now aligned.

Registration is a very important stage in the process of generating the change maps as it ensures when the arithmetic (point wise intensity subtraction) is calculated, the result will only show the change that has occurred because of the well operations and not due to grain/mineral misalignment.

2.2 Arithmetic Stage:—

The concept is A-B=C, in simple terms After minus Before equals Change.

This arithmetic function identifies all the changes from formation damaging mechanisms 12 caused during the above mentioned tests (for example the core flooding tests). Density alterations are made apparent by the difference between the A and B data sets 14A, 14B. Density alterations are typically caused by wellbore operations solids or wellbore operations filtrate retention. These formation damage mechanisms 12 can alter the pore network volume and this is indicated by density alterations (e.g. between the positive and negative changes).

The output created as part of the arithmetic function is a new data set which can be used to show change intensity. Change intensity is based on density alteration. Small alterations in density mean low change intensity and large alterations in density mean high change intensity.

2.3 Change Map Image Processing:—

Figure 6:
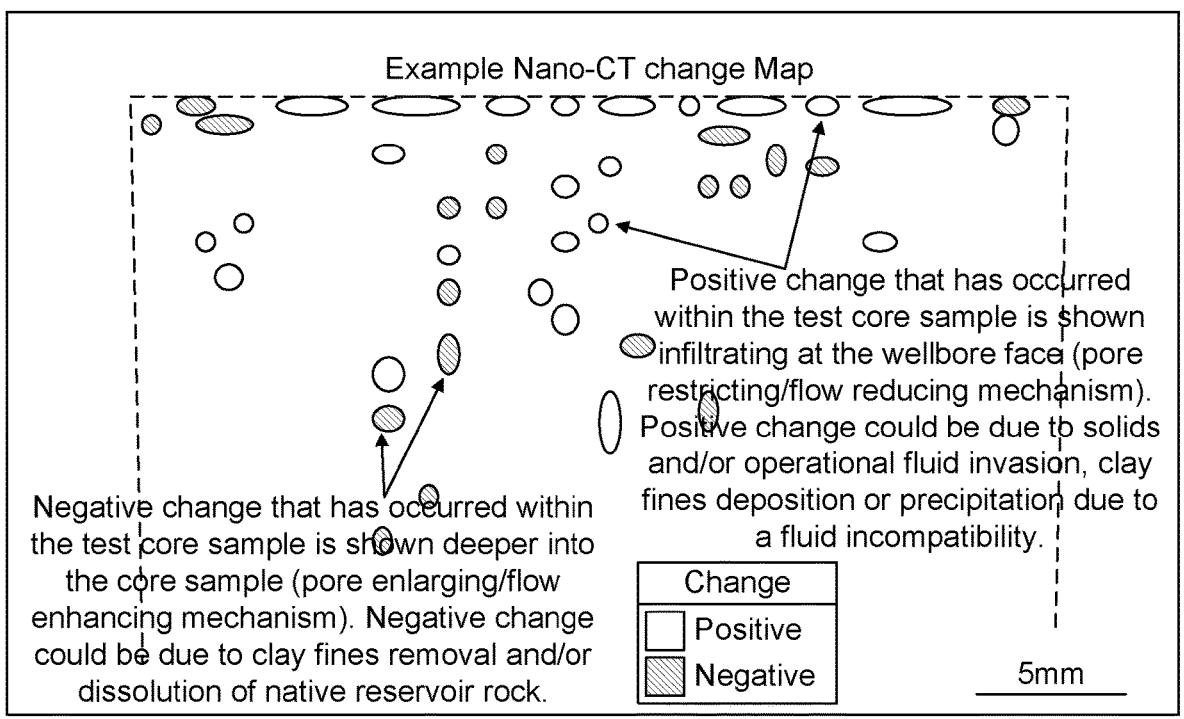
FIG. 6 schematically illustrates a nano-CT change map.

This stage involves processing the change intensity data to display a 3D volume representation of all the change that has occurred. Positive and negative change intensity can be separated as seen in the change map 24 shown in FIG. 6 (which includes examples of potential formation damage mechanisms that could cause the positive and negative change depicted).

Positive change which occurs as a result of pore restricting/flow reducing mechanism(s) could be due to solids and/or operational fluid invasion, clay fines deposition or precipitation due to a fluid incompatibility. Negative change which occurs as a result of pore enlarging/flow enhancing mechanism(s) could be due to clay fines removal and/or dissolution of native reservoir rock.

The change maps created are used to find specific areas of change that are of particular interest to the consultant at the up-scaling stage (i.e. the segmentation stage) later on in the investigation (see Stage 3 for more detail).

Figure 7:
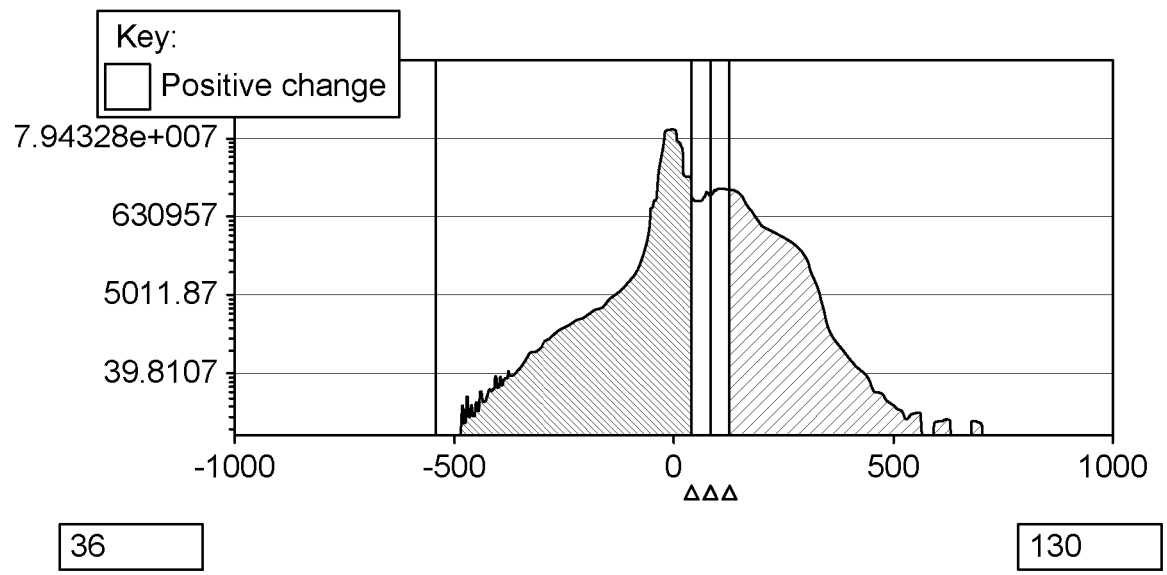
FIG. 7 schematically illustrates a positive change representative graph of the change map of FIG. 6.

Positive change can be displayed by adjusting the threshold value (e.g. 36-130 along the X axis in the graph shown in FIG. 7) allowing a 3D representation to be produced as shown in FIG. 17A. Threshold ranges vary from sample to sample because of the different density ranges e.g. some samples are denser than others.

Figure 8:
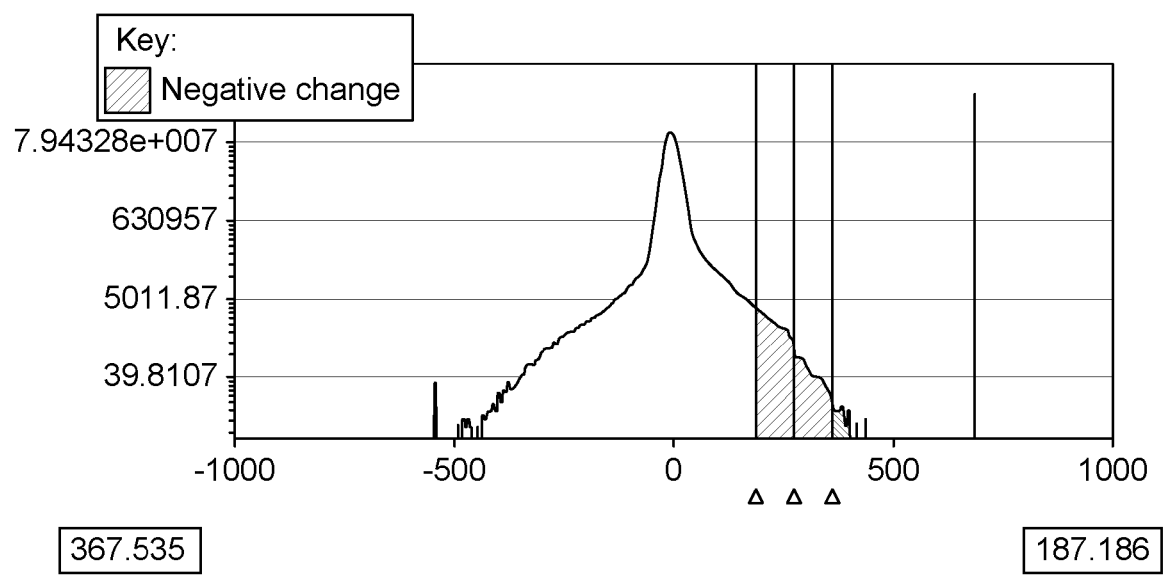
FIG. 8 schematically illustrates a negative change representative graph of the change map of FIG. 6.

Negative change can be obtained by inverting the change intensity spectrum allowing the consultant to adjust the threshold (e.g. 367-187 along the X axis in the graph shown in FIG. 8) allowing a 3D representation to be produced (as shown in FIG. 17B).

The change maps 24 created can then be quantified once the consultant is happy with the threshold values when further quality checks are made.

2.4 Quantification:—

This final stage involves calculating the total percentage of change regardless of intensity within a selected sub sample 101 to 116 and/or whole sample 10.

To allow the software to measure the change as a volume against the total volume of the selected sub sample and/or whole sample, a new data set is created using the binerization function.

Figure 9:
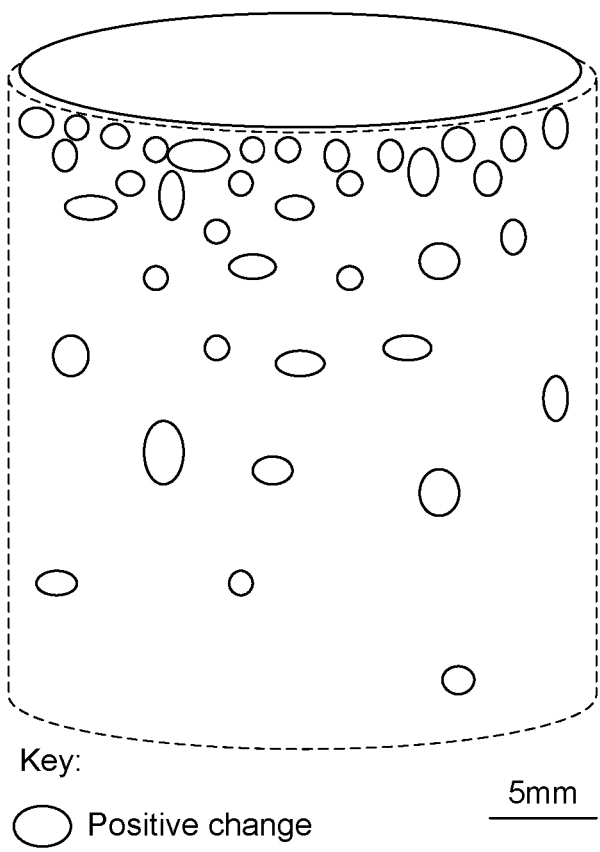
FIG. 9 schematically illustrates a volumetric representation of the new data set created for positive change (e.g. pore restricting flow reducing formation damaging mechanisms)

The change map 24 can be binerized to create a new data set from the threshold values above. When the change intensity data sets (positive change and negative change) are binerized both high and low intensity changes are attributed with a value of 1 and for no change attributed with a value of 0, meaning all change within the sample is accounted for. FIG. 9 shows a binerized data set for positive change (e.g. pore restricting flow reducing formation damaging mechanisms 12).

Once the new (binerized) data sets are created (positive change volume and negative change volume), the volume change percentage can be calculated. This is done using a function included with the imaging software which provides a volume for the change along with a whole volume. This means two separate change percentages can be created for positive and negative along with a total change percentage.

The positive and negative change volumes obtained at this point can be revisited at a later stage by the consultant at the up-scaling stage (i.e. the segmentation stage) of the investigation. This will involve sub-dividing the positive and negative change volumes into individual formation damage volumes (see Stage 3 for more detail), which can then be quantified as a percentage in order to determine the effect of the individual formation damage mechanisms 12.

Stage 3—Determining the Effect of Formation Damaging Mechanisms by Quantification of Formation Damage Mechanisms and their Effect on the Characteristics (e.g. Permeability) of a Core Sample (in Accordance with Step f))

The procedure for quantification of formation damage mechanism 12 and their effect on the characteristics (e.g. permeability) of the core sample 10 are outlined in more detail by the four sub-stages listed below:

3.1—Sub-sampling selected sub-samples from core sample 3.2—Very high resolution 3D dataset acquisition technique scanning of sub-samples and elemental analysis/chemical characterization of selected areas of interest 3.3—Registration of datasets 3.4—Generating a metrics database of the formation damaging mechanisms 3.1 Sub-Sampling Selected Sub-Samples from Core Sample for High Resolution 3D Dataset Acquisition Technique Scanning Following creation of the 3D change map, the consultant selects an appropriate number of sub-selected samples from within the core sample (from this point forward the sub-selected samples are described as 'cubes' although it is important to note that they need not be cube shaped but could be any suitable size and/or shape), and records the co-ordinates of the sub-selected 'cubes' that will be used to obtain even higher resolution datasets as will be subsequently described at stage 3.2. The cubes are selected from the specific areas of change that were of particular interest to the consultant as discussed above at stage 2.3. In other words, the consultant would not likely choose to conduct segmentation on "cubes" from a section of the drill core sample 10 which exhibited no change in the change maps.

Figure 10:
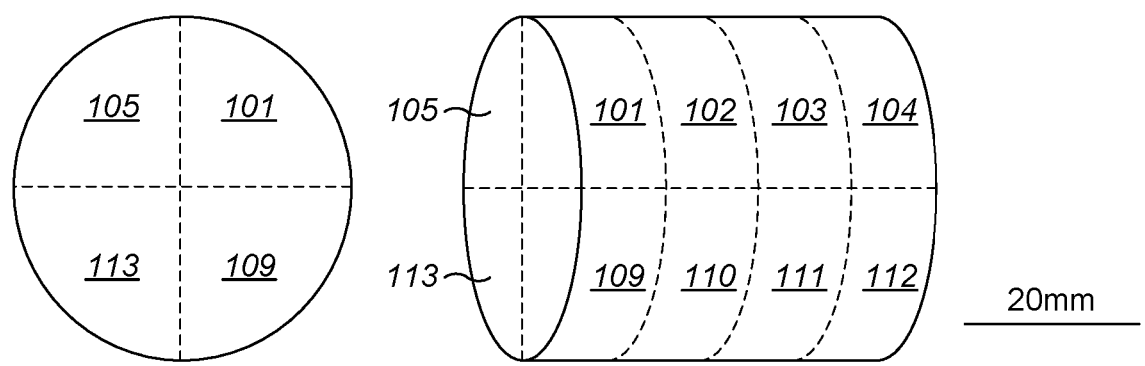
FIG. 10 schematically illustrates the marking of a core sample into an appropriate number of sub-selected samples.

Conveniently, 12-16 'cubes' are allocated from the core sample 10 to be sub-sampled and sixteen are provided in the embodiment as shown in FIG. 10 as cubes 101 to 116 (cubes 106 to 108 and cubes 114 to 116 being hidden from view).

It would be understood that the number of 'cubes' allocated is dependent on the size of the core sample 10.

The 'cubes' 101 to 116 are then either:—
a) physically cut from the core sample 10 using a core cutting tool into the allocated number of 'cubes' 101 to 116 from the exact locations coordinated (see FIG. 10) if for example a nano CT scan is conducted; or
b) selected as a zone of interest within the core sample 10 with the exact location being recorded if for example an XRM scan is conducted (in other words no physical cube need be cut but the scanning tool can zoom or zone in on the cube 101 to 116) whilst it is still an integral part of the core sample 10.

3.2 Very High Resolution 3D Dataset Acquisition Technique Scanning of Sub-Sampled 'Cubes' and Elemental Analysis/Chemical Characterization of Selected Areas of Interest Very high resolution 3D dataset acquisition technique scan datasets of each 'cube' are then obtained using a 3D dataset acquisition technique scanner, the very high resolution being an even higher resolution than that used in Stage 1 as described above.

Figure 5:
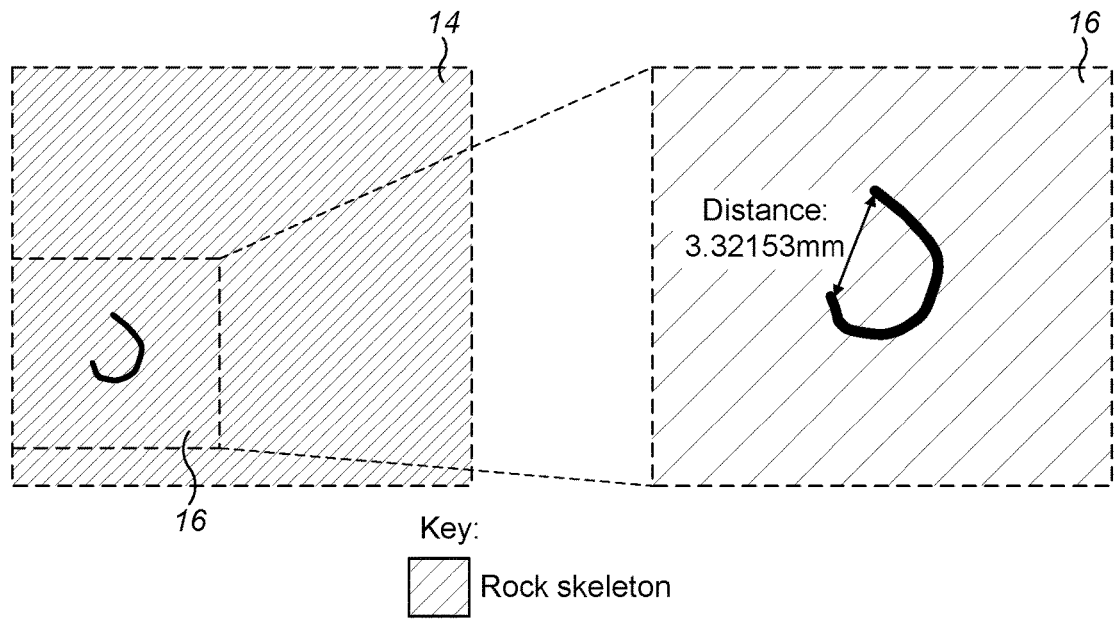
FIG. 5 schematically illustrates an example of a nano-CT scan data set where an area has been sub-selected for more detailed analysis.

The newly acquired datasets are then uploaded into a super-computer (not shown) and using a 3D image processing software, each very high resolution dataset (down to ~8

μm voxel size and preferably in the range of 0.5 μm to 10 μm voxel size for nano CT and between 0.1 μm to 5 μm for an XRM scan depending on the size of the zone of interest chosen is reviewed in order to carefully select an area of the respective 'cube' for elemental analysis/chemical characterization. FIG. 5 depicts an example of a 3D dataset acquisition technique scan data set 14 where an area 16 has been sub-selected for more detailed analysis.

The elemental analysis/chemical characterization may for example be performed by means of a Focus Ion Beam (FIB) device, a Scanning Electron Microscope (SEM) and/or an Energy-dispersive X-ray Spectroscopy (EDS) device. Preferably a Focussed Ion Beam Scanning Electron Microscope (FIB-SEM) is used in combination with an EDS device.

One area of interest is selected from each 'cube' 101 to 116 throughout the core sample (12-16 areas of interest in total). The co-ordinates of each area of interest is recorded at this stage to allow the consultant to register the FIB-SEM dataset with the corresponding 'cube' very high resolution 3D dataset acquisition technique scan dataset.

The selected areas of interest will then be analysed under the FIB-SEM/EDS instruments to allow even higher (i.e. ultra high) resolution imagery such as 0.001 μm to 0.5 μm (and preferably around 0.06 μm but further technical improvements in scanning techniques in future could allow even higher resolution than that) of a small stack of images and allow identification of the formation damaging mechanisms 12 (in accordance with step e)) that have occurred within the core sample 10 as a result of the well operations test sequence (for example the core flooding tests hereinbefore described during stage 1 and which were in accordance with step c)).

The FIB-SEM/EDS technique enables the consultant to acquire a chemical element map of the area of interest selected therefore identifying the formation damage mechanisms present.

This stage can generate individual or combinations of 3D skeletons representing formation damage mechanism(s), grain(s) and pore space(s) by segmentation (water shedding).

Segmentation (Also Known as "Watershedding")

At this point, it is useful to explain that segmentation involves separating individual components of a rock or an object; in more simple terms this involves separating a single solid piece of rock into individual components (Grains, clays and pore space).

Figure 11A:
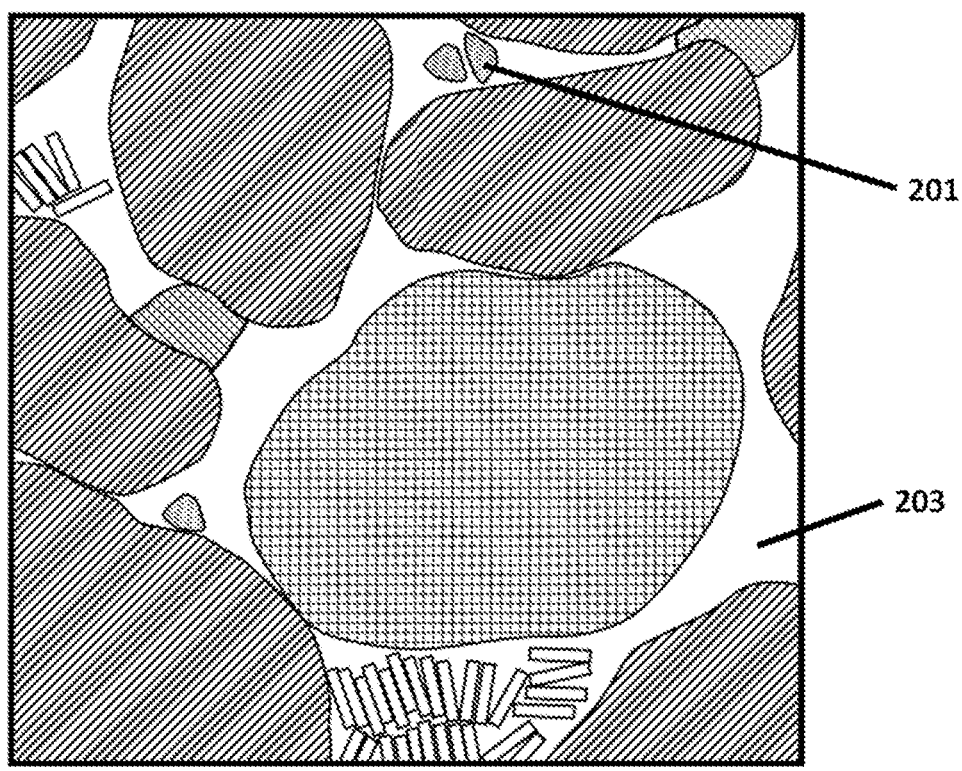
FIG. 11A is a greyscale image produced from a micro-CT or nano-CT scan of a 2D slice of a cube 101-106 during segmentation.

Micro-CT or Nano CT scanning is conducted on the drill core sample 10 (and in particular on one or more or more preferably all of the cubes 101 to 116) such that the operator acquires a series of 2D slices in the X, Y and Z axis. These 2D slices depict at greyscale an image which is based on X-ray attentuation. X-ray attentuation is based on the x-ray strength, x-ray path length, material density and atomic number of the material in the path of/detected by the x-ray. As shown in FIG. 11A, denser materials with high atomic numbers will cause the highest grayscale values (white in colour and marked with reference number 201 in FIG. 11A), the lowest greyscale values (black in colour and marked with reference numeral 203 in FIG. 11A) include material which is low in density.

Each value range in the greyscale image corresponds to a different material such as a mineral, clay or fluid; see the example given in FIG. 11A. Using the different greyscale threshold values, each assigned material can be segmented and attributed to a new phase. These individual phases could be separate; phase 1, 2, 3, 4 and 5. Alternatively, some phases could be grouped as a single phase; phase 1+2, 3, 4+5, now making 3 phases.

In summary, segmentation separates each phase based on the greyscale range (threshold value), and these individual phases can be grouped forming a new phase if so required. Or additionally, a single greyscale phase can be edited to remove unwanted objects, such as clays. Chlorite and Kaolinite clays potentially will fall under the same greyscale value, depending on the quality of the image contrast produced during scanning. These two morphically different clays will need to be adjusted, so they are separated. This can be done by making two identical data sets and removing all the Kaolinite clay from one and all the chlorite clay from the other.

Figure 11B:
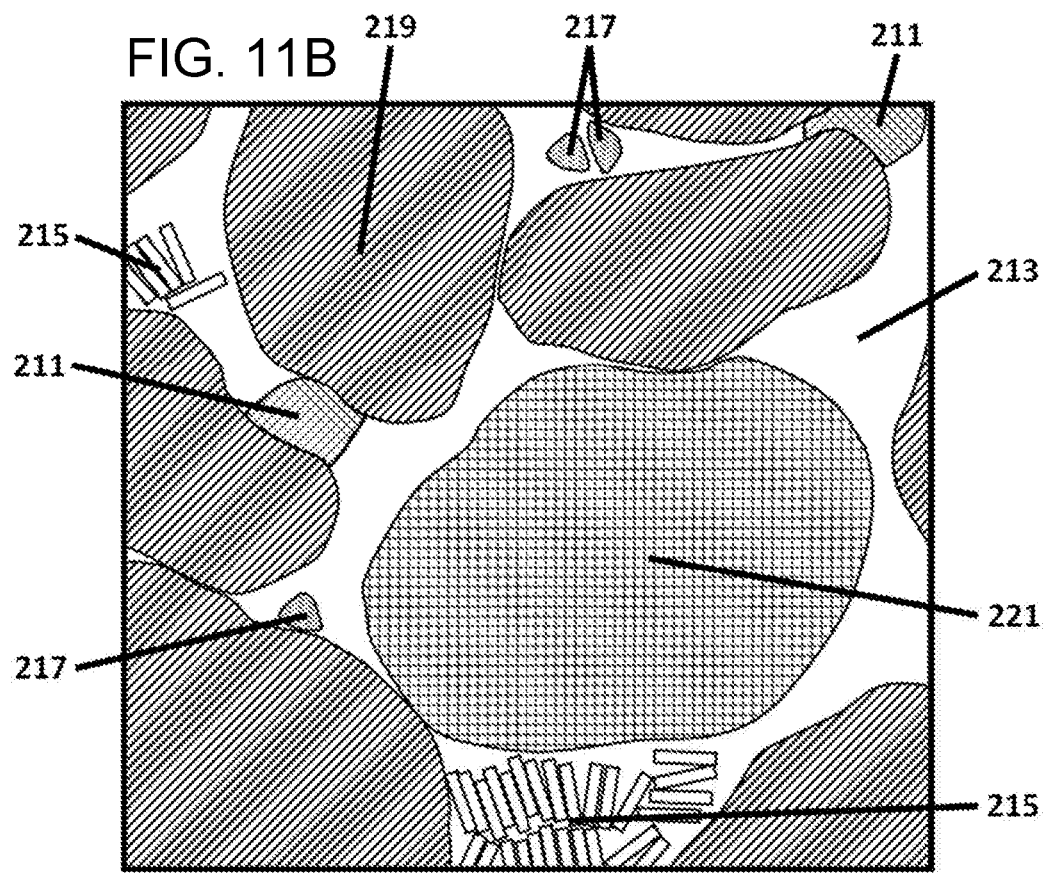
FIG. 11B is a colour version of the greyscale image of FIG. 11A where each colour represents a different material of the 2D slice of the cube 101-106 shown in the greyscale image of FIG. 11A.
Figure 11C:
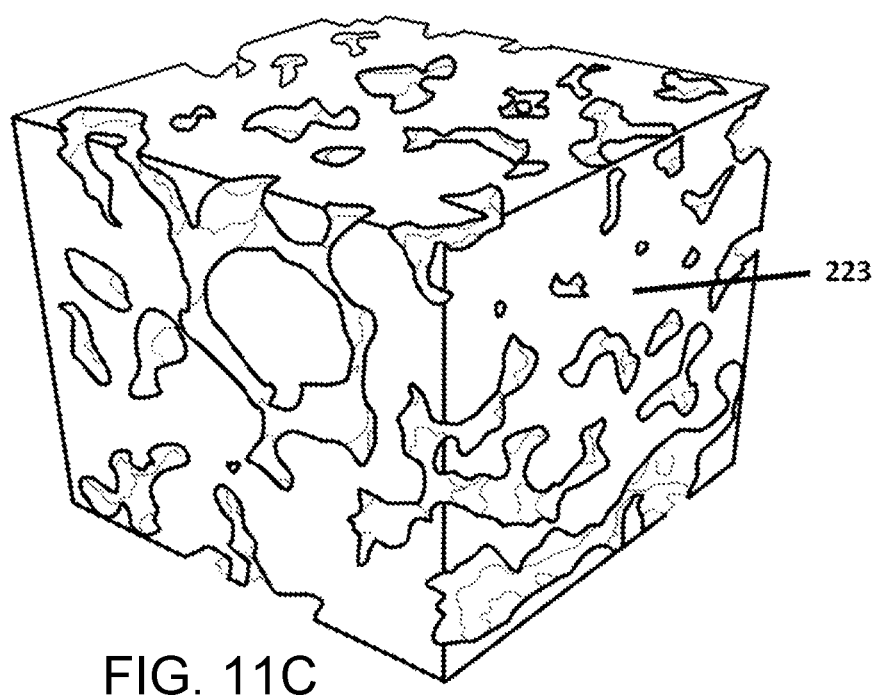
FIG. 11C is produced during segmentation and represents the unchanged rock skeleton 223 of the cube 101-106 and is created in suitable computer software from all the colour images produced from all the respective 2D slices such as that shown in FIG. 11A taken of the cube 101-106 and is comprised of the Purple 219+Yellow 221+unchanged Green 215 components.
Figure 11D:
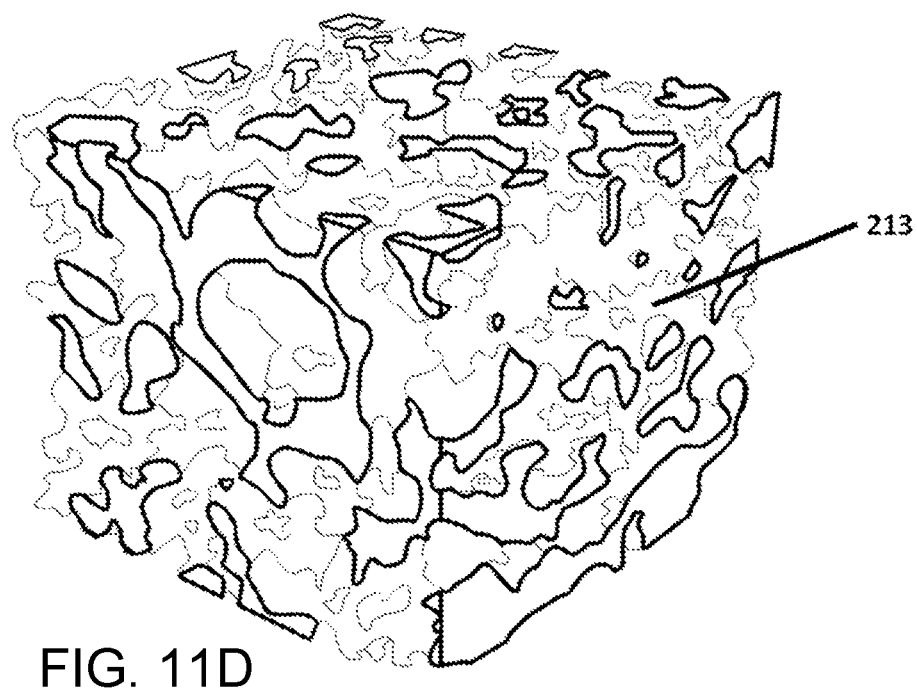
FIG. 11D is produced during segmentation and represents the unrestricted open pore network of the cube 101-106 and is created in suitable computer software from all the colour images produced from all the respective 2D slices such as that shown in FIG. 11A taken of the cube 101-106, where the open pore network is open to the flow of brine 213 comprised of the Blue 213 component.
Figure 11E:
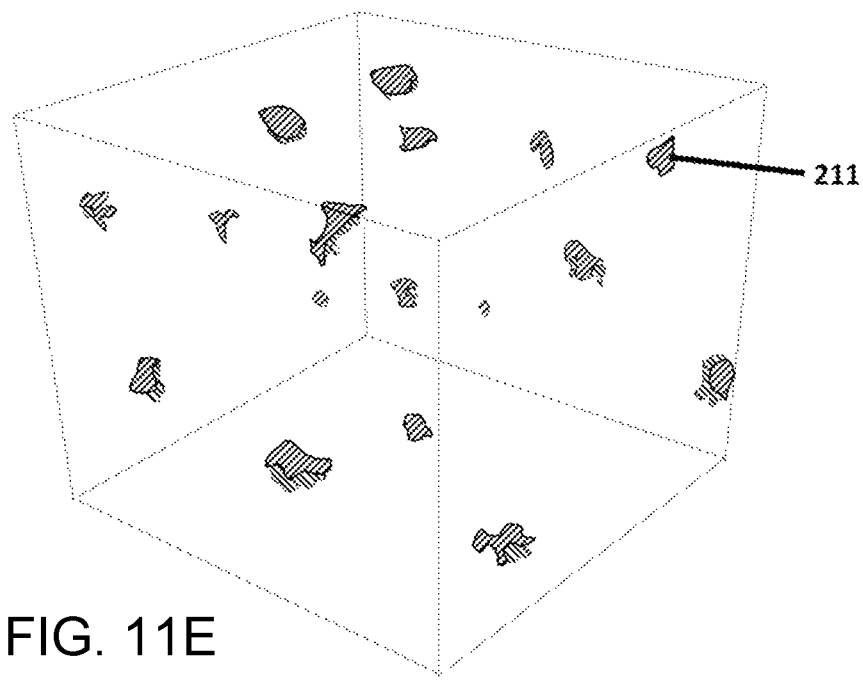
FIG. 11E is produced during segmentation and represents the oil based mud filtrate 211 of the cube 101-106 and is created in suitable computer software from all the colour images produced from all the respective 2D slices such as that shown in FIG. 11A taken of the cube 101-106, where the mud filtrate 211 is comprised of the Red component 211.
Figure 11F:
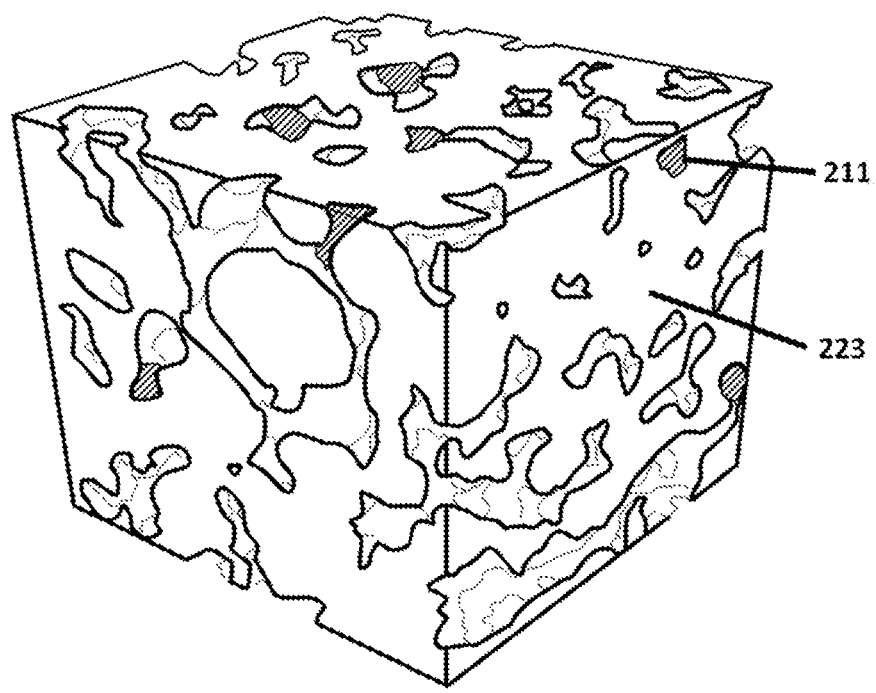
FIG. 11F is produced during segmentation and represents the oil based mud filtrate 211 comprised of the Red 211 component added into the pore network of the unchanged rock skeleton of the cube 101-106 and is created in suitable computer software from all the colour images produced from all the respective 2D slices such as that shown in FIG. 11A taken of the cube 101-106.
Figure 11G:
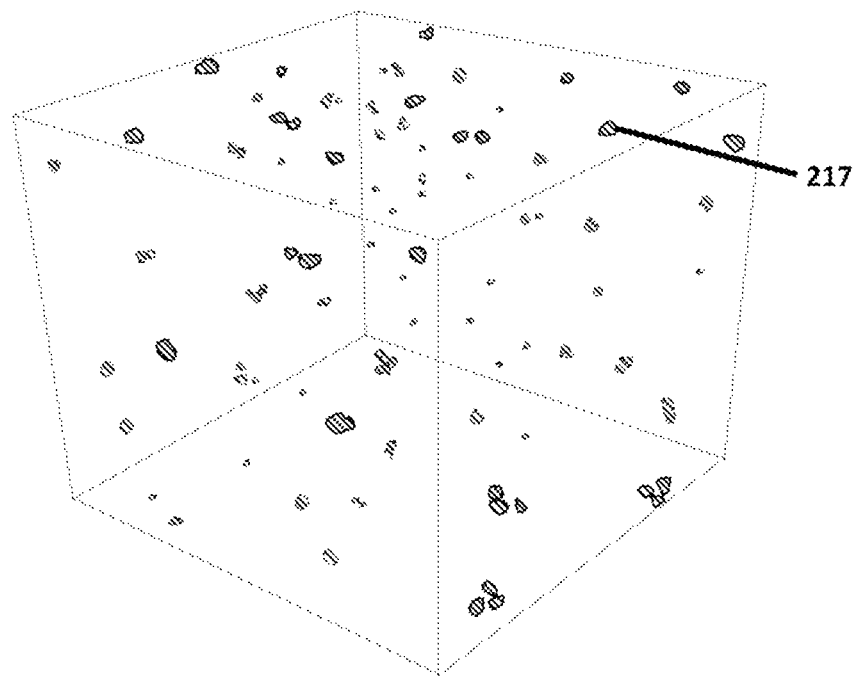
FIG. 11G is produced during segmentation and represents the drilling mud solids 217 of the cube 101-106 and is created in suitable computer software from all the colour images produced from all the respective 2D slices such as that shown in FIG. 11A taken of the cube 101-106, where the drilling mud solids 217 are comprised of the Orange 217 component.
Figure 11H:
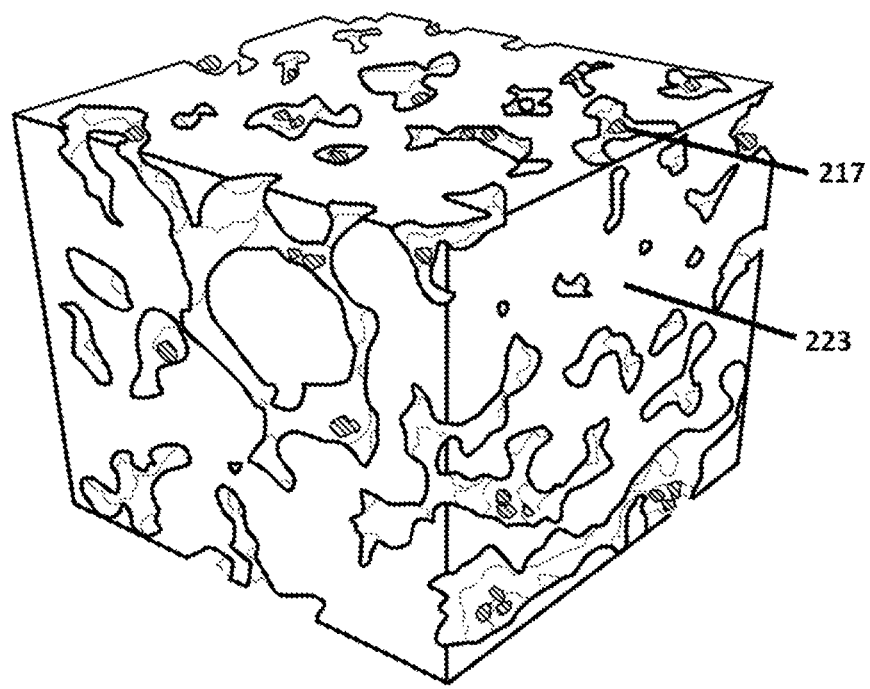
FIG. 11H is produced during segmentation and represents the drilling mud solids 217 comprised of the Orange 217 component added into the pore network of the unchanged rock skeleton of the cube 101-106 and is created in suitable computer software from all the colour images produced from all the respective 2D slices such as that shown in FIG. 11A taken of the cube 101-106.
Figure 11I:
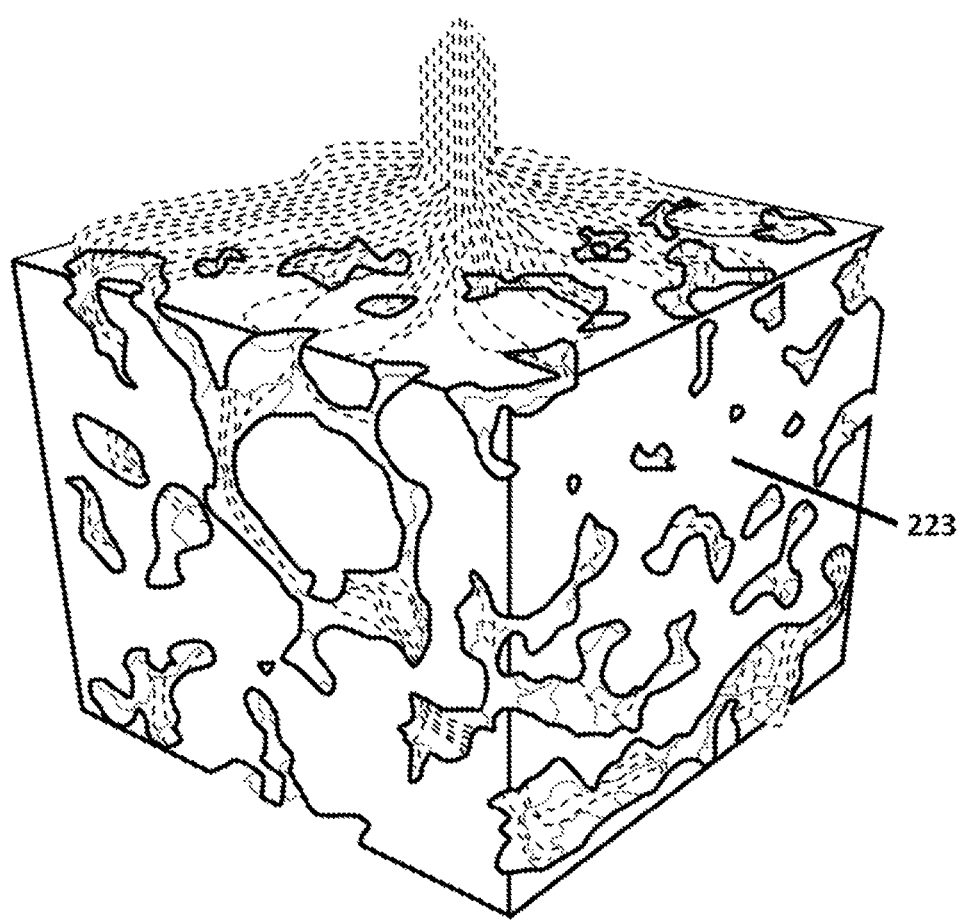
FIG. 11I is produced during segmentation and represents a permeability simulation created in suitable computer software and is based upon all the colour images produced from all the respective 2D slices such as that shown in FIG. 11A taken of the cube 101-106, where the permeability simulation could include the unchanged rock 223 only=base line measurement. or alternatively, simulations with the rock skeleton 223 and permeability reducing components (formation damage) for permeability based metrics.
Figure 11J:
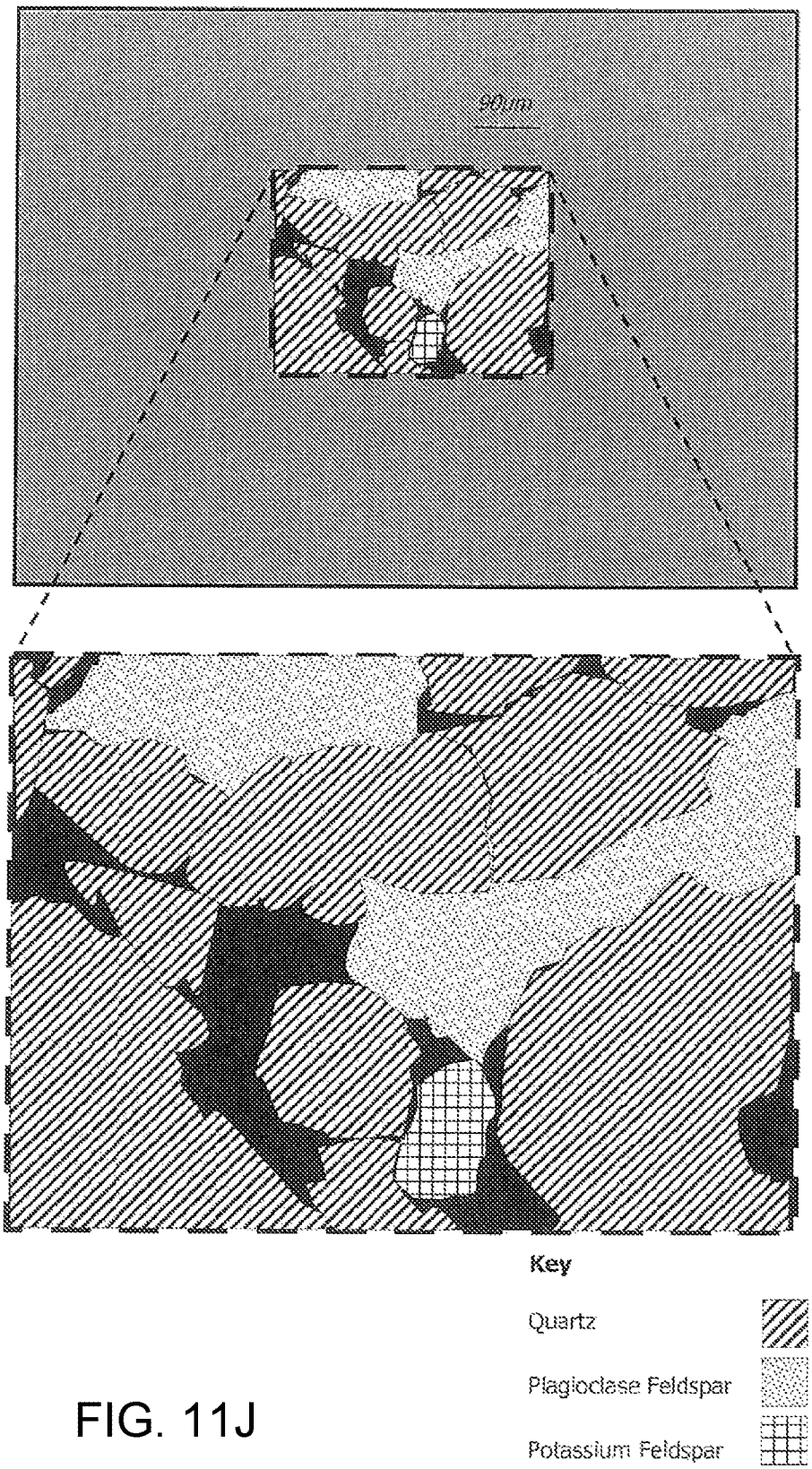
FIG. 11J schematically illustrates an example of a nano-CT scan created during a segmentation image depicting detrital grains (8 μm voxel size)

Once all the phases have been separated into individual volume data sets, these can be depicted using a selected colour pallet, see the image in FIG. 11B in which the following colours have been assigned the following reference numbers for the purposes of this patent specification and which relate to the following materials:—

Red 211=oil based mud filtrate;
Blue 213=brine;
Green 215=Kaolinite clay;
Orange 217=drilling mud solids;
Purple 219=Quartz grains; and
Yellow 221=Feldspar grains.

It should be noted that in this example, Purple 219 and yellow 221 components make the native skeleton. The green 215 component if unchanged during a core flood test would also be included into the native rock skeleton (Purple 219+Yellow 221+unchanged Green 215=Rock Skeleton). These components will be grouped for later permeability simulations. The blue 213 represents the open pore space (pore network) for the flowing phase, which in this example would be brine 213. The brine 213 will flow through the rock skeleton; permeability will change depending on the addition of certain components (which could be formation damage). The red 211, orange 217 and changed green 215 components would be the formation damage mechanisms. Adding or taking away these components from the pore network will change the flow paths through the pore network. Adding these components will reduce and impede flow thus causing permeability to drop.

Purple 219+Yellow 221+unchanged Green 215=Unrestricted flow,maximum/optimum flow potential Purple 219+Yellow 221+unchanged Green 215+Red 211=Restricted flow Purple 219+Yellow 221+unchanged Green 215+Red 211+Orange 217+changed Green 215=Restricted flow, worse case flow potential.

In summary, the aim of segmentation is to prevent the reduction of blue 213, with the addition of the orange 217 and reds 211 which cause the drop in blue 213.

3.3 Registration of FIB-SEM/EDS and 3D Dataset Acquisition Technique Scan Datasets Following acquisition of the FIB-SEM/EDS chemical element maps from each area of interest, these high resolution datasets are uploaded to the 3D image processing software along with the corresponding dataset of the very high resolution 'cube' 3D dataset acquisition technique scan.

The software needs to be capable of reading any binary volume of data. The software will register the two datasets before further processing is performed. This involves fine tuning functions for filtering and boundary interfacing via the 'water shedding' or segmentation stage described above at paragraph 3.2.

A materials structure imaging tool within the software or a 3D visualization and analysis software for exploring core sample 10 and digital rock data sets, for example Avizo® Fire, will be used for upscaling to extrapolate the formation damaging mechanisms 12 captured in the FIB-SEM/EDS small area of interest to have similar occurrences rendered elsewhere throughout the remainder of the corresponding 3D 'cube' dataset.

FIG. 12A illustrates an example of an ultra high resolution 500× magnification SEM image region and FIG. 12B illustrates a registered region of a 3D scanned image.

FIG. 13 illustrates an example of filtering and boundary interfacing via 'water shedding' which allows for upscaling to extrapolate the formation damaging mechanisms 12 captured in the FIB-SEM/EDS small area of interest (FIG. 13a—before 'water shedding'; FIG. 13b—after 'water shedding').

3.4 Generating a Metrics Database of the Formation Damaging Mechanisms for the Core Sample Once the formation damage mechanisms 12 have been rendered throughout each 'cubed' dataset ('water shedding' or segmentation complete), the consultant can use the software to calculate the percentage volume of each formation damage mechanism 12, for example fines accumulation, drilling solid retention.

Figure 14:
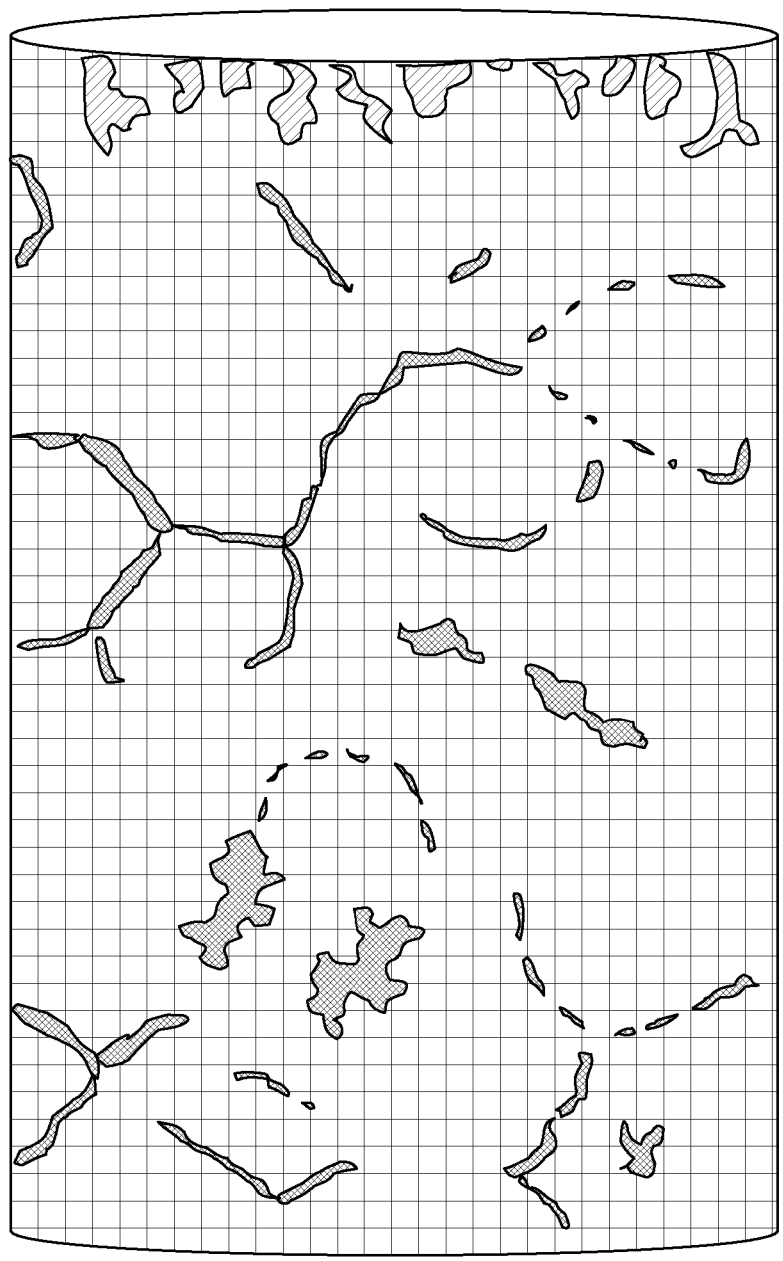
FIG. 14 shows a schematic diagram that illustrates the result of 'watershed segmentation'.

For each 'cube' 101 to 116, a table can be populated that lists the formation damage mechanisms 12 and the percentage volume change. This generates a database for all the 'cubes' 101 to 116. From this database any query can be executed e.g. grouping the percentage volume of clay fines migration from each 'cube' 101 to 116. FIG. 14 shows a schematic diagram that illustrates the result of 'watershed segmentation' which allows for quantification of the separate phases.

Further value to the database on formation damage mechanisms 12 may be added by generating additional characteristics (e.g. permeability) metrics as described below.

Figure 15:
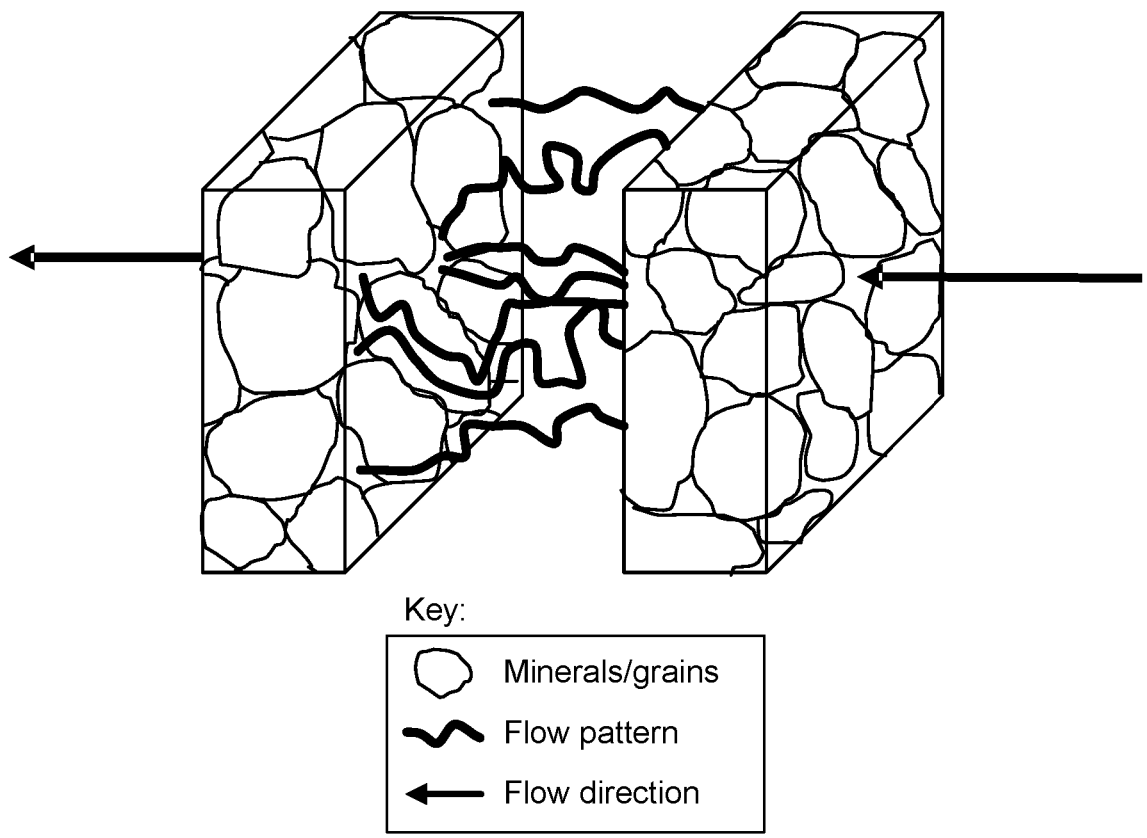
FIG. 15 schematically illustrates an example of fluid flow through a porous medium depicting the technique used to measure the characteristics (e.g. permeability) of a porous medium.

Using a software package capable of performing numerical simulations from calculated characteristics (e.g. permeability) of a porous media from a scanned core sample 10, for example Avizo® XLab Hydro extension, the consultant can generate characteristics (e.g. permeability) metrics on each 'cube' 101 to 116. FIG. 15 shows an example of fluid flow through a porous medium depicting the technique used to measure the characteristics (e.g. permeability) of a porous medium.

The algorithm used in the software should be Darcy's Law which is the industry standard algorithm for measuring permeability. This initial permeability metric is generated with all formation damaging mechanisms 12 present in the first 'cube' 101. For each 'cube' 101 to 116 the consultant or software user will then mask/threshold out some of the formation damaging mechanisms 12 so that the permeability can be measured with only individual or combinations of formation damaging mechanisms 12 present. All permeability metrics can then be added to the metrics database on formation damage mechanisms 12 which presents the option of performing queries to group selected formation damage mechanisms 12 or permeabilities.

Figure 16:
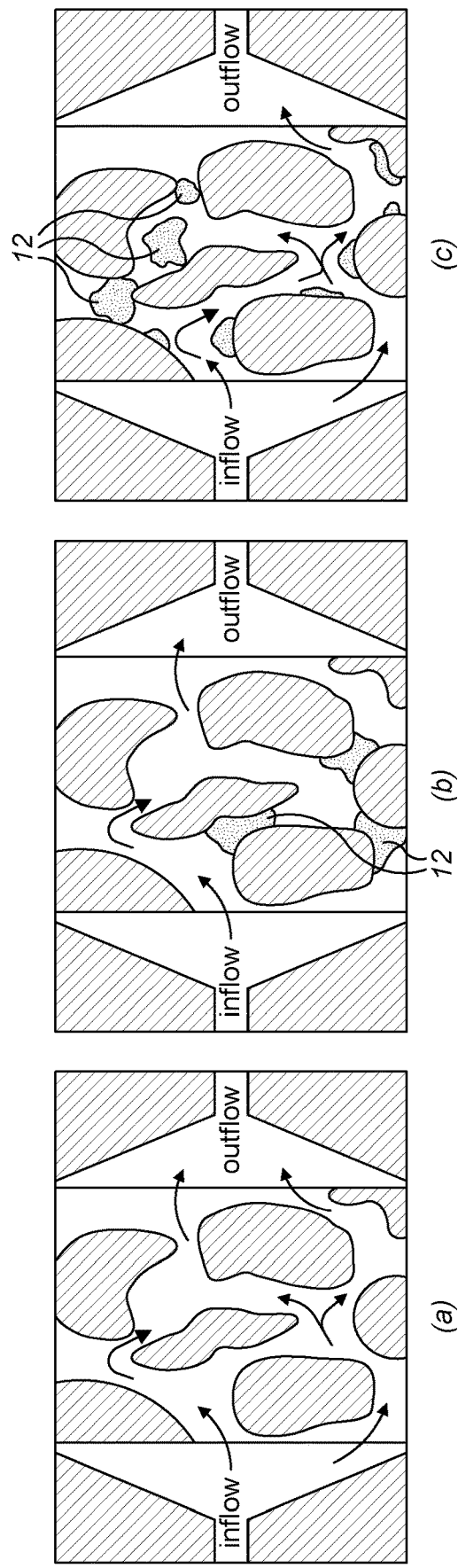
FIG. 16 schematically illustrates the effects on characteristics (e.g. permeability) by the presence of formation damaging mechanisms.

FIG. 16 shows the simulation of characteristics (e.g. permeability) measurements of individual damaging mechanisms 12 with (a) no damaging mechanisms present, (b) clay fines migration only, and (c) fluid retention only.

Following construction of a database and use of subsequent queries, a consultant may choose to rank variables e.g. fluid products or fluid sequence applications based on either the total volume of formation damage mechanisms 12 and/or characteristics (e.g. permeability). The consultant can then use this database to see how much of an influence each formation damage mechanism 12 has on the characteristics (e.g. permeability) (in accordance with step f)). For example; the effect on the characteristics (e.g. permeability) of pore restricting clay fines migration or separately pore enlarging clay fines migration could be reviewed. The following decisions could thus be made based on the query findings:

a) Use new wellbore operations;
b) Modify wellbore operations;
c) Not perform wellbore operations (terminating);
d) Take no action and continue as planned.

Below is an example (non-exclusive) list of formation damage mechanisms 12 that may be recorded in the database:

i) Fines migration (e.g. clays, precipitates, plankton debris, microbes, polymers);
ii) Dissolution of mineral matrix and cavitations/collapse of formation or pore volume compaction;
iii) Wellbore Operation Fluids invasion with subsequent retention (e.g., solids entrapment and/or filtrate retention);
iv) Phase entrapment (e.g., polymer adsorption onto the skeletal grains reducing pore volume);
v) Precipitates (organic and/or inorganic from either fluid/fluid and/or fluid/fluid/rock interactions—Pore fluids and Injected fluids);
vi) Emulsions;
vii) Asphaltenes deposition;
viii) Wax deposition;
ix) Bacterial fouling and cell growth; etc.

It is apparent that embodiments of the present the invention, as described above, also advantageously provide a method of quantification of formation damage mechanisms in a subterranean drilled core sample and the effect of the formation damage mechanisms on the characteristics (e.g. permeability) of the core sample 10.

It has been found that the most significant gains in terms of risk-reduction come when an "integrated approach" is taken,
  design tests that are an accurate simulation of the operations or conditions under consideration;
  perform the testing, gathering data which typically consists of characteristics (e.g. permeability) measurements, pressure measurements, and sample images; and
  understand laboratory test results through quantitative interpretative analysis that allows alterations in the samples to be put in context and conclusions/recommendations made.

Consequently, embodiments of the present invention disclosed hereinbefore teach assigning each piece of change (ie each damage mechanism 12) to its own skeleton along with the rock skeleton (ie everything in the core structure which didn't change) and that then can be used to provide a number of different skeletons in the software. Furthermore, constructing a new skeleton of the unchanged skeleton plus the skeleton created by the first damage mechanism 12 (for example fines migration) can then be used to inform the operator/consultant the percentage volume or mass change, etc. Furthermore, by conducting a simulation or virtual measurement of the characteristic of the core sample 10 of interest (for example the permeability or the porosity) on each of the new skeletons can inform the operator/consultant how the e.g. permeability or porosity has changed or behaved for each formation damage mechanism 12.

Whilst prior art analysis methods could inform an operator what the total change (e.g. reduction) in the permeability of a core sample 10 is, embodiments of the present invention have the very great advantage that not only do they inform an operator what the total change in the permeability or porosity of a core sample 10 is, they also crucially can inform the operator or consultant what the permeability or porosity measurements of each formation damage mechanism 12 is. This is very advantageous because one formation damage mechanism can influence one or more other formation damage mechanisms and therefore knowing exactly what the effect of each individual formation damage mechanism is can give the operator or consultant far greater insight than just knowing what the total effect on e.g. the permeability has been.

As an example, the total reduction in permeability for a tested core sample 10=−53.4%

Embodiments of the present invention therefore have the great advantage that they can also inform the operator or consultant what the metric is for each individual formation damage mechanism 12 is = for example, $1^{st}$ Formation damage mechanism reduction=−10.3%
$2^{nd}$ Formation damage mechanism reduction=−16.7%
$3^{rd}$ Formation damage mechanism reduction=−17.3%
$4^{th}$ Formation damage mechanism reduction=−9.1%

Figure 18:
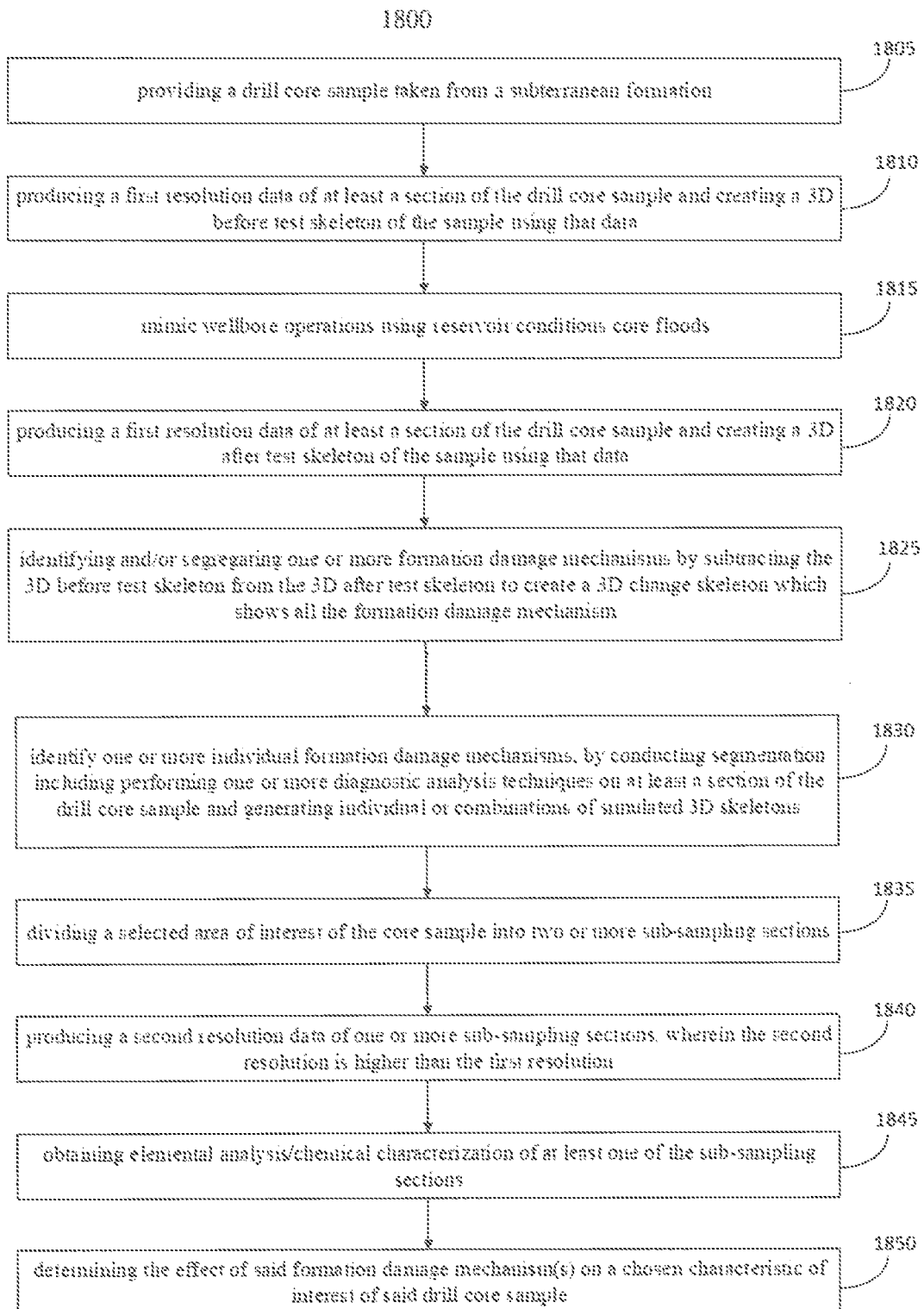
FIG. 18 schematically illustrates a method according to an example embodiment.

FIG. 18 is a flowchart illustrating a method 1800 of an example embodiment. Method 1800 comprises, at step 1805 providing a drill core sample taken from a subterranean formation. Step 1810 comprises producing a first resolution data of at least a section of the drill core sample and creating a 3D before test skeleton of the sample using that data. Step 1815 comprises mimic wellbore operations using reservoir conditions core floods. Step 1820 comprises producing a first resolution data of at least a section of the drill core sample and creating a 3D after test skeleton of the sample using that data. Step 1825 comprises identifying and/or segregating one or more formation damage mechanisms by subtracting the 3D before test skeleton from the 3D after test skeleton to create a 3D change skeleton which shows all the formation damage mechanisms. Step 1830 comprises identify one or more individual formation damage mechanisms, by conducting segmentation including performing one or more diagnostic analysis techniques on at least a section of the drill core sample and generating individual or combinations of simulated 3D skeletons. Step 1835 comprises dividing a selected area of interest of the core sample into two or more sub-sampling sections. Step 1840 comprises producing a second resolution data of one or more sub-sampling sections, wherein the second resolution is higher than the first resolution. Step 1845 comprises obtaining elemental analysis/chemical characterization of at least one of the sub-sampling sections. Step 1850 comprises determining the effect of said formation damage mechanism(s) on a chosen characteristic of interest of said drill core sample.

Figure 19:
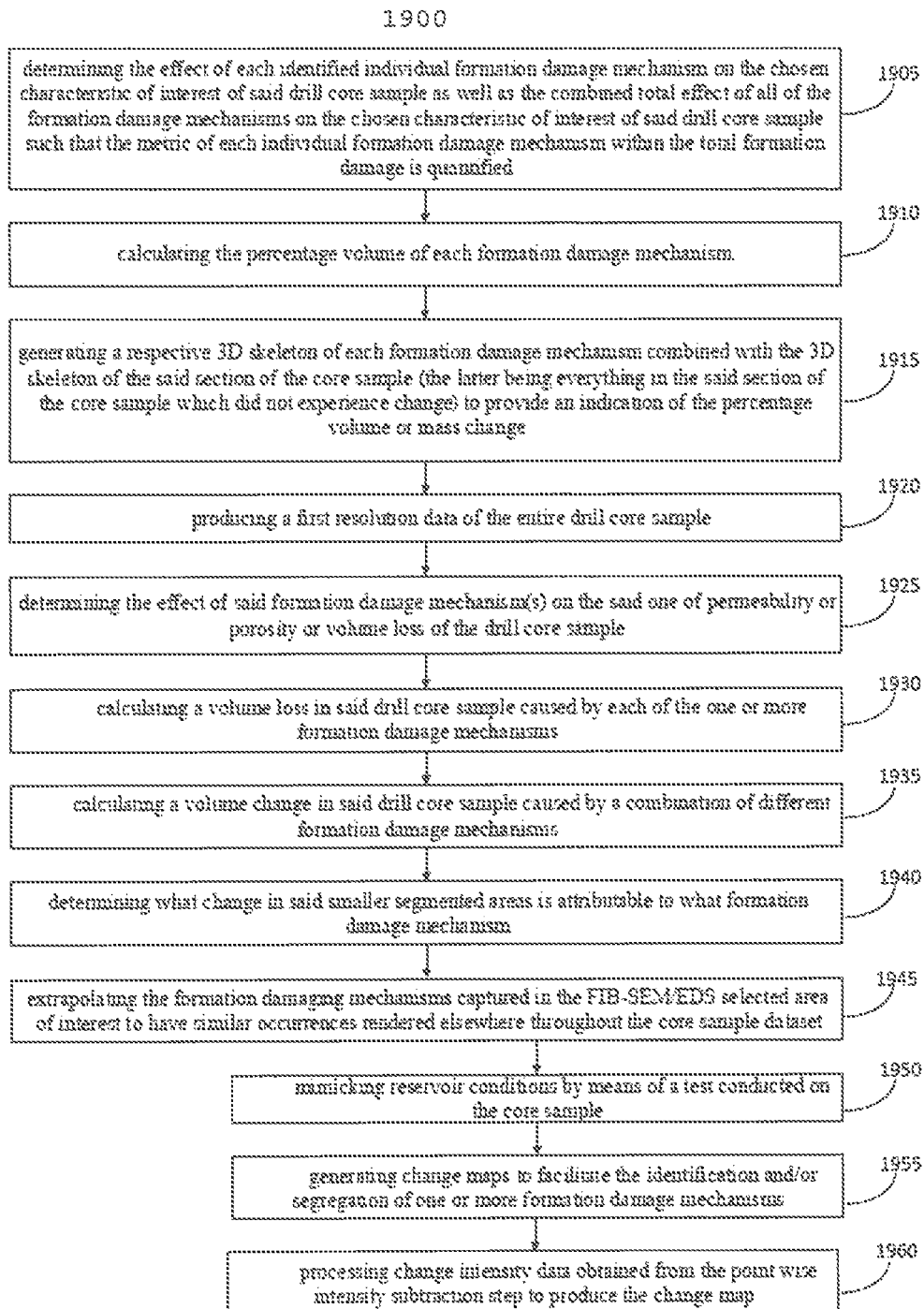
FIG. 19 schematically illustrates a method according to an example embodiment.

FIG. 19 is a flowchart illustrating potential method steps according to an example embodiment. Step 1905 comprises determining the effect of each identified individual formation damage mechanism on the chosen characteristic of interest of said drill core sample as well as the combined total effect of all of the formation damage mechanisms on the chosen characteristic of interest of said drill core sample such that the metric of each individual formation damage mechanism within the total formation damage is quantified. Step 1910 comprises calculating the percentage volume of each formation damage mechanism. Step 1915 comprises generating a respective 3D skeleton of each formation damage mechanism combined with the 3D skeleton of the said section of the core sample (the latter being everything in the said section of the core sample which did not experience change) to provide an indication of the percentage volume or mass change. Step 1920 comprises producing a first resolution data of the entire drill core sample. Step 1925 comprises determining the effect of said formation damage mechanism(s) on the said one of permeability or porosity or volume loss of the drill core sample. Step 1930 comprises calculating a volume loss in said drill core sample caused by each of the one or more formation damage mechanisms. Step 1935 comprises calculating a volume change in said drill core sample caused by a combination of different formation damage mechanisms. Step 1940 comprises determining what change in said smaller segmented areas is attributable to what formation damage mechanism. Step 1945 comprises extrapolating the formation damaging mechanisms captured in the FIB-SEM/EDS selected area of interest to have similar occurrences rendered elsewhere throughout the core sample dataset. Step 1950 comprises mimicking reservoir conditions by means of a test conducted on the core sample. Step 1955 comprises generating change maps to facilitate the identification and/or segregation of one or more formation damage mechanisms. Step 1960 comprises processing change intensity data obtained from the point wise intensity subtraction step to produce the change map.

Modifications and improvements may be made to the embodiments hereinbefore described without departing from the scope of protection.

The invention claimed is:
1. A method of analysing a subterranean drilled core sample, comprising:
 a) providing a drill core sample taken from a subterranean formation;
 b) producing a first resolution data of at least a section of the drill core sample and creating a 3D before test skeleton of the sample using that data;
 c) mimic wellbore operations using reservoir conditions core floods;
 d) producing a first resolution data of at least a section of the drill core sample and creating a 3D after test skeleton of the sample using that data;
 e) identifying and/or segregating one or more formation damage mechanisms by subtracting the 3D before test skeleton from the 3D after test skeleton to create a 3D change skeleton which shows all the formation damage mechanisms; and
 f) 1) identify one or more individual formation damage mechanisms, by conducting segmentation including performing one or more diagnostic analysis techniques on at least a section of the drill core sample and generating individual or combinations of simulated 3D skeletons;
  i) dividing a selected area of interest of the core sample into two or more sub-sampling sections,
  ii) producing a second resolution data of one or more sub-sampling sections, wherein the second resolution is higher than the first resolution, and
  iii) obtaining elemental analysis/chemical characterization of at least one of the sub-sampling sections wherein iii) obtaining elemental analysis/chemical characterization of at least one of the sub-sampling sections further comprises determining what change in said smaller segmented areas is attributable to what formation damage mechanism, and further comprises:
  iv) constructing further 3D skeletons comprising a combination of the 3D change skeleton of step e) being combined with one or more of the simulated 3D skeletons of step f) 1);
  and
    2) determining the effect of said formation damage mechanism(s) on a chosen characteristic of interest of said drill core sample.

2. A method according to claim 1, wherein step f) 2) further comprises determining the effect of each identified individual formation damage mechanism on the chosen characteristic of interest of said drill core sample as well as the combined total effect of all of the formation damage mechanisms on the chosen characteristic of interest of said drill core sample such that the metric of each individual formation damage mechanism within the total formation damage quantified.

3. A method according to claim 1, wherein said determining step f) further comprises calculating the percentage volume of each formation damage mechanism.

4. A method according to claim 1 wherein step f) 1) further comprises generating a respective 3D skeleton of each formation damage mechanism combined with the 3D skeleton of the said section of the core sample (the latter being everything in the said section of the core sample which did not experience change) to provide an indication of the percentage volume or mass change.

5. A method according to claim 1, wherein the 3D skeletons are computer generated and the effect of said formation damage mechanisms is determined through the use of computer based permeability simulations on the said computer generated 3D skeletons of said drill core sample.

6. A method according to claim 1, wherein step b) and/or step d) comprises producing a first resolution data of the entire drill core sample.

7. A method according to claim 1, wherein the chosen characteristic of interest comprises one of permeability or porosity or volume change such that step f) comprises determining the effect of said formation damage mechanism(s) on the said one of permeability or porosity or volume loss of the drill core sample.

8. A method according to claim 7, wherein said determining step f) further comprises calculating a volume loss in said drill core sample caused by each of the one or more formation damage mechanisms.

9. A method according to claim 7, wherein said determining step f) further comprises calculating a volume change in said drill core sample caused by a combination of different formation damage mechanisms.

10. A method according to claim 7, wherein the formation damage mechanism includes fines accumulation and/or drilling solid retention.

11. A method according to claim 1, wherein the core sample is divided into 12-16 sub-sampling sections.

12. A method according to claim 1, wherein the first resolution data of step b) and/or step d) is produced by a suitable 3D dataset acquisition method.

13. A method according to claim 12, wherein the 3D dataset acquisition method comprises nano CT scanning, XRM, FIB, micro CT scanning or synchrotron analysis.

14. A method according to claim 1, wherein the elemental analysis/chemical characterization of step f) iii) is obtained by a Focussed Ion Beam Scanning Electron Microscope (FIB-SEM) used in combination with an Energy-dispersive X-ray Spectroscopy device (EDS).

15. A method according to claim 14, further comprising the step of extrapolating the formation damaging mechanisms captured in the FIB-SEM/EDS selected area of interest to have similar occurrences rendered elsewhere throughout the core sample dataset.

16. A method according to claim 1, wherein features of the sub-sampling sections in the second resolution data of step f) ii) and features of the sub-sampling section obtained from data derived from the elemental analysis/chemical characterization of step f) iii) are matched via registration or point matching.

17. A method of quantification of formation damage mechanisms in a subterranean drilled core sample and the effect of the formation damage mechanisms on the characteristics of the core sample comprising the steps of analysing a subterranean drilled core sample in accordance with claim 1.

18. A method according to claim 17, wherein the characteristics of the core sample includes the permeability of the core sample.

19. A method of analysing a subterranean drilled core sample, comprising:
  a) providing a drill core sample taken from a subterranean formation;
  b) producing a first resolution data of at least a section of the drill core sample and creating a 3D before test skeleton of the sample using that data;
  c) mimic wellbore operations using reservoir conditions core floods;
  d) producing a first resolution data of at least a section of the drill core sample and creating a 3D after test skeleton of the sample using that data;
  e) identifying and/or segregating one or more formation damage mechanisms by subtracting the 3D before test skeleton from the 3D after test skeleton to create a 3D change skeleton which shows all the formation damage mechanisms; and
  f) 1) identify one or more individual formation damage mechanisms, by conducting segmentation including performing one or more diagnostic analysis techniques on at least a section of the drill core sample and generating individual or combinations of simulated 3D skeletons;
    i) dividing a selected area of interest of the core sample into two or more sub-sampling sections,
    ii) producing a second resolution data of one or more sub-sampling sections, wherein the second resolution is higher than the first resolution, and
    iii) obtaining elemental analysis/chemical characterization of at least one of the sub-sampling sections
  and
    2) determining the effect of said formation damage mechanism(s) on a chosen characteristic of interest of said drill core sample
wherein the second resolution data of step f) is produced by a suitable 3D dataset acquisition method.

20. A method of analysing a subterranean drilled core sample, comprising:
  a) providing a drill core sample taken from a subterranean formation;
  b) producing a first resolution data of at least a section of the drill core sample and creating a 3D before test skeleton of the sample using that data;
  c) mimic wellbore operations using reservoir conditions core floods;

d) producing a first resolution data of at least a section of the drill core sample and creating a 3D after test skeleton of the sample using that data;
e) identifying and/or segregating one or more formation damage mechanisms by subtracting the 3D before test skeleton from the 3D after test skeleton to create a 3D change skeleton which shows all the formation damage mechanisms; and
f) 1) identify one or more individual formation damage mechanisms, by conducting segmentation including performing one or more diagnostic analysis techniques on at least a section of the drill core sample and generating individual or combinations of simulated 3D skeletons;
  i) dividing a selected area of interest of the core sample into two or more sub-sampling sections,
  ii) producing a second resolution data of one or more sub-sampling sections, wherein the second resolution is higher than the first resolution, and
  iii) obtaining elemental analysis/chemical characterization of at least one of the sub-sampling sections
and
  2) determining the effect of said formation damage mechanism(s) on a chosen characteristic of interest of said drill core sample wherein step c) comprises mimicking reservoir conditions by means of a test conducted on the core sample
wherein one or more first resolution after test data sets and/or scans of the entire drill core sample are produced at step d) after the reservoir conditions test of step c)
wherein change maps are generated to facilitate the identification and/or segregation of one or more formation damage mechanisms in step e)
wherein the process of generating the change maps comprises the following steps:
  over laying and aligning the before and after test data sets;
  point wise intensity subtraction of the after test data sets from the before test data sets;
  change map image processing to produce a change map; and
  quantification of the data and change map.

21. A method according to claim 20, wherein the test conducted on the core sample is a core flooding test.

22. A method according to claim 20, wherein first resolution data of the entire drill core sample is produced prior to the reservoir conditions test of step c) at step b) in order to produce before test data sets and/or scans.

23. A method according to claim 20, wherein first resolution after test data sets and/or scans are further additionally produced during various further stages of the test sequence depending on objectives in order to produce one or more after test data sets and/or scans as part of step e).

24. A method according to claim 20, wherein the change map image processing step comprises processing change intensity data obtained from the point wise intensity subtraction step to produce the change map.

25. A method according to claim 24, wherein positive and negative change intensity are separated in the change map.

26. A method according to claim 20, wherein the quantification of the data and change map comprises the creation of a new data set using a binerization function.

27. A method of analysing a subterranean drilled core sample, comprising:
  a) providing a drill core sample taken from a subterranean formation;
  b) producing a first resolution data of at least a section of the drill core sample and creating a 3D before test skeleton of the sample using that data;
  c) mimic wellbore operations using reservoir conditions core floods;
  d) producing a first resolution data of at least a section of the drill core sample and creating a 3D after test skeleton of the sample using that data;
  e) identifying and/or segregating one or more formation damage mechanisms by subtracting the 3D before test skeleton from the 3D after test skeleton to create a 3D change skeleton which shows all the formation damage mechanisms; and
  f) 1) identify one or more individual formation damage mechanisms, by conducting segmentation including performing one or more diagnostic analysis techniques on at least a section of the drill core sample and generating individual or combinations of simulated 3D skeletons; and
    2) determining the effect of said formation damage mechanism(s) on a chosen characteristic of interest of said drill core sample;
  wherein step f) 2) further comprises determining the effect of each identified individual formation damage mechanism on the chosen characteristic of interest of said drill core sample as well as the combined total effect of all of the formation damage mechanisms on the chosen characteristic of interest of said drill core sample such that the metric of each individual formation damage mechanism within the total formation damage is quantified.

28. A method of analysing a subterranean drilled core sample, comprising:
  a) providing a drill core sample taken from a subterranean formation;
  b) producing a first resolution data of at least a section of the drill core sample and creating a 3D before test skeleton of the sample using that data;
  c) mimic wellbore operations using reservoir conditions core floods;
  d) producing a first resolution data of at least a section of the drill core sample and creating a 3D after test skeleton of the sample using that data;
  e) identifying and/or segregating one or more formation damage mechanisms by subtracting the 3D before test skeleton from the 3D after test skeleton to create a 3D change skeleton which shows all the formation damage mechanisms; and
  f) 1) identify one or more individual formation damage mechanisms, by conducting segmentation including performing one or more diagnostic analysis techniques on at least a section of the drill core sample and generating individual or combinations of simulated 3D skeletons; and
    2) determining the effect of said formation damage mechanism(s) on a chosen characteristic of interest of said drill core sample;
  wherein said determining step f) 2) further comprises calculating the percentage volume of each formation damage mechanism.

29. A method of analysing a subterranean drilled core sample, comprising:
  a) providing a drill core sample taken from a subterranean formation;
  b) producing a first resolution data of at least a section of the drill core sample and creating a 3D before test skeleton of the sample using that data;

c) mimic wellbore operations using reservoir conditions core floods;
d) producing a first resolution data of at least a section of the drill core sample and creating a 3D after test skeleton of the sample using that data;
e) identifying and/or segregating one or more formation damage mechanisms by subtracting the 3D before test skeleton from the 3D after test skeleton to create a 3D change skeleton which shows all the formation damage mechanisms; and
f) 1) identify one or more individual formation damage mechanisms, by conducting segmentation including performing one or more diagnostic analysis techniques on at least a section of the drill core sample and generating individual or combinations of simulated 3D skeletons; and generating a respective 3D skeleton of each formation damage mechanism combined with the 3D skeleton of the said section of the core sample (the latter being everything in the said section of the core sample which did not experience change) to provide an indication of the percentage volume or mass change; and
   2) determining the effect of said formation damage mechanism(s) on a chosen characteristic of interest of said drill core sample.

30. A method of analysing a subterranean drilled core sample, comprising:
a) providing a drill core sample taken from a subterranean formation;
b) producing a first resolution data of at least a section of the drill core sample and creating a 3D before test skeleton of the sample using that data;
c) mimic wellbore operations using reservoir conditions core floods;
d) producing a first resolution data of at least a section of the drill core sample and creating a 3D after test skeleton of the sample using that data;
e) identifying and/or segregating one or more formation damage mechanisms by subtracting the 3D before test skeleton from the 3D after test skeleton to create a 3D change skeleton which shows all the formation damage mechanisms; and
f) 1) identify one or more individual formation damage mechanisms, by conducting segmentation including performing one or more diagnostic analysis techniques on at least a section of the drill core sample and generating individual or combinations of simulated 3D skeletons; and
   2) determining the effect of said formation damage mechanism(s) on a chosen characteristic of interest of said drill core sample;
wherein the said 3D skeletons are computer generated and the effect of said formation damage mechanisms is determined through the use of computer based permeability simulations on the said computer generated 3D skeletons of said drill core sample.

\* \* \* \* \*